United States Patent
Robinson et al.

(10) Patent No.: US 6,703,542 B1
(45) Date of Patent: Mar. 9, 2004

(54) POLYPHENOL OXIDASE GENES

(75) Inventors: Simon Piers Robinson, Hyde Park (AU); Ian Barry Dry, Melrose Park (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 08/482,934

(22) Filed: Jun. 7, 1995

Related U.S. Application Data

(62) Division of application No. 08/182,045, filed as application No. PCT/AU92/00356 on Jul. 16, 1992.

(30) Foreign Application Priority Data

Jul. 17, 1991 (AU) .............................................. PK7248

(51) Int. Cl.$^7$ .......................... A01H 5/00; C12N 15/82; C07H 21/02
(52) U.S. Cl. .................... 800/286; 800/298; 435/252.3; 435/320.1; 435/468; 536/25.1
(58) Field of Search ................................ 800/205, 278, 800/284, 286, 287, 298; 435/69.1, 172.3, 419, 468, 430, 252.2, 252.3, 320.1, 25.1; 536/23.6, 23.1

(56) References Cited

U.S. PATENT DOCUMENTS

| 4,940,835 A | 7/1990 | Shah |
| 6,160,204 A | 12/2000 | Steffens |

FOREIGN PATENT DOCUMENTS

| JP | 62205783 | 9/1987 |
| WO | 8802372 | 4/1988 |
| WO | WO-A-89/11227 | 11/1989 |
| WO | 9315599 | 8/1993 |

OTHER PUBLICATIONS

Vander Krol et al., (1988) Nature 333:866–869 (Exhibit 6).
Finnegan et al., (1994) Biotechnology, 12:883–888 (Exhibit 7).
Matsuoka et al. (Feb. 1991), Proc. Natl Acad Sci. USA 88: 834–838 (Exhibit 8).
Ohara et al., (1989) Proc. Natl Acad Sci. USA 86:5673–5677 (Exhibit 9).
Twell et al. (1987) Plant Mol Biol. 9:345–375 (Exhibit 10).
Williams et al., Abstract of the Annual Meeting of the American Society for Microbiology–90th Meeting, p. 163, 1990.
Shahar, et al., "The Tomato 663–kD Polyphenoloxidase Gene: Molecular Identification and Developmental Expression", *The Plant Cell*, Feb. 1992.
Cary, et al., "Cloning and Characterisation of a gene presumed to encode polyphenol oxidase", *Plant Physiology*, vol. 93, p. 41, (1990) Abstract Nr. 230.
Steffens, et al., "Cloning of glandular trichome polyphenol oxidase", *Plant Physiology*, vol. 93, p. 15, (1990) Abstract Nr. 82.
Hunt, et al., "A functional analysis of poly phenol oxidase (PPO) in Solanum–tuberosum using sense and antisense genes", *Plant Physiology*, vol. 99, p. 88, (1992) Abstract Nr. 526.
Batistuti, et al., "Isolation and purification of polyphenoloxidase from a new variety of potato", *Food Chemistry*, vol. 18, pp. 251–263, (1985).
Van Der Krol, et al., "Antisense genes in plants: an overview", *Gene*, vol. 72, pp. 45–50, (1988).

*Primary Examiner*—Elizabeth F. McElwain
(74) *Attorney, Agent, or Firm*—John P. White; Cooper & Dunham LLP

(57) ABSTRACT

A DNA sequence including a gene coding polypeptide having polyphenol oxidase (PPO) activity, or a fragment thereof.

21 Claims, 15 Drawing Sheets

FIGURE 1-1

```
         10        20        30        40        50        60
          |         |         |         |         |         |
ATCACTCATCACTCCTCCTCTAAAGCTATGGCTTCTTTGCCTTGGTCGCTCACAACCTCC
                           M  A  S  L  P  W  S  L  T  T  S 70        80        90       100       110       120
          |         |         |         |         |         |
ACCGCCATCGCCAACACCACCAACATTTCAGCCTTCCCACCTTCTCCCTTGTTTCAAAGG
 T  A  I  A  N  T  T  N  I  S  A  F  P  P  S  P  L  F  Q  R 130       140       150       160       170       180
          |         |         |         |         |         |
GCTTCTCATGTCCCCGTAGCCAGAAACCGAAGCCGCAGATTTGCTCCTAGTAAGGTGTCG
 A  S  H  V  P  V  A  R  N  R  S  R  R  F  A  P  S  K  V  S 190       200       210       220       230       240
          |         |         |         |         |         |
TGCAATTCTGCGAATGGTGATCCCAACTCGGATTCTACCTCCGACGTTCGAGAAACTTCC
 C  N  S  A  N  G  D  P  N  S  D  S  T  S  D  V  R  E  T  S 250       260       270       280       290       300
          |         |         |         |         |         |
TCAGGGAAGTTAGATAGGAGGAATGTGCTTCTTGGCATAGGAGGGCTGTATGGTGCTGCT
 S  G  K  L  D  R  R  N  V  L  L  G  I  G  G  L  Y  G  A  A 310       320       330       340       350       360
          |         |         |         |         |         |
GGCGGTCTCGGCGCCACTAAGCCATTAGCCTTTGGGGCTCCCATCCAGGCACCGGATATA
 G  G  L  G  A  T  K  P  L  A  F  G  A  P  I  Q  A  P  D  I
                                     * ---------------------

370       380       390       400       410       420
          |         |         |         |         |         |
TCCAAGTGTGGTACCGCCACCGTGCCTGATGGTGTAACGCCCACAAATTGCTGCCCGCCA
 S  K  C  G  T  A  T  V  P  D  G  V  T  P  T  N  C  C  P  P
------------

430       440       450       460       470       480
          |         |         |         |         |         |
GTCACCACAAAGATTATAGATTTCCAGCTACCTTCCTCAGGTTCCCCCATGCGTACCAGG
 V  T  T  K  I  I  D  F  Q  L  P  S  S  G  S  P  M  R  T  R
```

FIGURE 1-2

```
         490       500       510       520       530       540
          |         |         |         |         |         |
CCAGCTGCTCACTTGGTCAGCAAAGAGTACTTAGCCAAGTATAAAAAGGCCATTGAGCTG
 P  A  A  H  L  V  S  K  E  Y  L  A  K  Y  K  K  A  I  E  L 550       560       570       580       590       600
          |         |         |         |         |         |
CAGAAAGCTCTTCCTGATGATGATCCGCGTAGTTTCAAGCAACAGGCTAATGTCCATTGC
 Q  K  A  L  P  D  D  D  P  R  S  F  K  Q  Q  A  N  V  H  C 610       620       630       640       650       660
          |         |         |         |         |         |
ACCTATTGCCAAGGGGCTTATGATCAGGTTGGGTATACCGACCTAGAACTCCAGGTTCAT
 T  Y  C  Q  G  A  Y  D  Q  V  G  Y  T  D  L  E  L  Q  V  H 670       680       690       700       710       720
          |         |         |         |         |         |
GCTTCATGGCTTTTCCTCCCTTTCCACCGTTACTATCTCTACTTCAATGAGAGAATTCTT
 A  S  W  L  F  L  P  F  H  R  Y  Y  L  Y  F  N  E  R  I  L 730       740       750       760       770       780
          |         |         |         |         |         |
GCAAAGTTGATCGACGATCCCACCTTCGCTTTGCCCTATTGGGCTTGGGATAACCCTGAT
 A  K  L  I  D  D  P  T  F  A  L  P  Y  W  A  W  D  N  P  D 790       800       810       820       830       840
          |         |         |         |         |         |
GGCATGTATATGCCGACCATCTATGCTAGTTCCCCATCATCACTCTACGACGAGAAGCGC
 G  M  Y  M  P  T  I  Y  A  S  S  P  S  S  L  Y  D  E  K  R 850       860       870       880       890       900
          |         |         |         |         |         |
AACGCCAAGCACCTGCCTCCGACTGTGATCGATCTCGACTACGATGGCACCGAACCCACA
 N  A  K  H  L  P  P  T  V  I  D  L  D  Y  D  G  T  E  P  T 910       920       930       940       950       960
          |         |         |         |         |         |
ATCCCTGATGACGAACTAAAAACCGACAATCTGGCAATCATGTACAAACAAATTGTGTCG
 I  P  D  D  E  L  K  T  D  N  L  A  I  M  Y  K  Q  I  V  S 970       980       990      1000      1010      1020
          |         |         |         |         |         |
GGTGCCACGACTCCTAAGCTTTTCCTTGGTTACCCATACCGCGCCGGCGATGCGATTGAC
 G  A  T  T  P  K  L  F  L  G  Y  P  Y  R  A  G  D  A  I  D
```

FIGURE 1-3

```
          1030      1040      1050      1060      1070      1080
            |         |         |         |         |         |
CCTGGAGCGGGTACCCTTGAGCACGCCCCACATAATATAGTCCACAAATGGACTGGTCTT
  P  G  A  G  T  L  E  H  A  P  H  N  I  V  H  K  W  T  G  L 1090      1100      1110      1120      1130      1140
            |         |         |         |         |         |
GCTGATAAGCCTAGTGAGGACATGGGAAACTTCTATACTGCCGGCAGAGACCCCATATTC
  A  D  K  P  S  E  D  M  G  N  F  Y  T  A  G  R  D  P  I  F 1150      1160      1170      1180      1190      1200
            |         |         |         |         |         |
TTCGGTCACCACGCCAATGTCGATCGGATGTGGAATATATGGAAAACTATAGGAGGTAAA
  F  G  H  H  A  N  V  D  R  M  W  N  I  W  K  T  I  G  G  K 1210      1220      1230      1240      1250      1260
            |         |         |         |         |         |
AATAGAAAGGATTTCACGGATACGGATTGGCTTGACGCCACGTTCGTCTTCTACGACGAG
  N  R  K  D  F  T  D  T  D  W  L  D  A  T  F  V  F  Y  D  E 1270      1280      1290      1300      1310      1320
            |         |         |         |         |         |
AACAAACAACTTGTTAAAGTCAAGGTCTCGGACTGTGTCGACACTTCCAAGCTGAGATAC
  N  K  Q  L  V  K  V  K  V  S  D  C  V  D  T  S  K  L  R  Y 1330      1340      1350      1360      1370      1380
            |         |         |         |         |         |
CAATATCAGGATATTCCTATTCCATGGCTACCAAAAAATACGAAGGCCAAAGCGAAGACG
  Q  Y  Q  D  I  P  I  P  W  L  P  K  N  T  K  A  K  A  K  T 1390      1400      1410      1420      1430      1440
            |         |         |         |         |         |
ACCACCAAAAGTTCCAAGTCGGGAGTAGCGAAAGCGGCCGAACTCCCAAAGACGACGATC
  T  T  K  S  S  K  S  G  V  A  K  A  A  E  L  P  K  T  T  I 1450      1460      1470      1480      1490      1500
            |         |         |         |         |         |
AGCAGCATCGGAGACTTCCCAAAAGCTCTTAACTCAGTGATAAGAGTAGAAGTTCCAAGG
  S  S  I  G  D  F  P  K  A  L  N  S  V  I  R  V  E  V  P  R 1510      1520      1530      1540      1550      1560
            |         |         |         |         |         |
CCAAAGAAATCAAGAAGCAAGAAGGAGAAAGAGGATGAGGAAGAGGTGTTACTGATAAAA
  P  K  K  S  R  S  K  K  E  K  E  D  E  E  E  V  L  L  I  K
```

FIGURE 1-4

```
        1570       1580       1590       1600       1610       1620
          |          |          |          |          |          |
GGAATAGAGCTAGATAGAGAGAATTTCGTGAAGTTTGATGTGTACATCAACGACGAAGAT
  G  I  E  L  D  R  E  N  F  V  K  F  D  V  Y  I  N  D  E  D 1630       1640       1650       1660       1670       1680
          |          |          |          |          |          |
TATTCAGTGAGTAGGCCTAAGAATAGTGAGTTTGCAGGAAGCTTTGTGAACGTACCACAC
  Y  S  V  S  R  P  K  N  S  E  F  A  G  S  F  V  N  V  P  H 1690       1700       1710       1720       1730       1740
          |          |          |          |          |          |
AAGCATATGAAAGAAATGAAGACGAAGACCAATCTGAGGTTCGCGATAAATGAGCTGTTA
  K  H  M  K  E  M  K  T  K  T  N  L  R  F  A  I  N  E  L  L 1750       1760       1770       1780       1790       1800
          |          |          |          |          |          |
GAGGACTTGGGAGCCGAAGATGATGAGAGTGTGATCGTGACTATAGTCCCTCGTGCTGGG
  E  D  L  G  A  E  D  D  E  S  V  I  V  T  I  V  P  R  A  G 1810       1820       1830       1840       1850       1860
          |          |          |          |          |          |
GGCGATGATGTCACCATTGGTGGAATTGAGATCGAGTTTGTTTCCGATTGATCCATCTT
  G  D  D  V  T  I  G  G  I  E  I  E  F  V  S  D  -

1870       1880       1890       1900       1910       1920
          |          |          |          |          |          |
TCAATGATTATCCATTATATGTATGTATCAGGTAAGTCACATCTTTATGTGATTAATGGA 1930       1940       1950       1960       1970       1980
          |          |          |          |          |          |
AAATGTGAGACTTCTCTGTACTTTCCCGTCAAGTCTTTTATTAATTTAGAGCGTTGGTTA

1990
          |
AAAAAAAAAA
```

FIGURE 2-1

```
         10        20        30        40        50        60
          |         |         |         |         |         |
TTTTACGATGAGAACAAGAATCTTGTTAGGGTTAATGTGAAGGACAGTCTTGACACAGAA
 F  Y  D  E  N  K  N  L  V  R  V  N  V  K  D  S  L  D  T  E 70        80        90       100       110       120
          |         |         |         |         |         |
AAACTAGGTTATGCTTATCAAAATGTTCCCATTCCATGGGAAAATGCTAAACCTGTGCCA
 K  L  G  Y  A  Y  Q  N  V  P  I  P  W  E  N  A  K  P  V  P 130       140       150       160       170       180
          |         |         |         |         |         |
CGAAGAACAAAAGTACCAAAATTGGTGGAAGTTGAGGTTAATGATGGAAACTTAAGAAAA
 R  R  T  K  V  P  K  L  V  E  V  E  V  N  D  G  N  L  R  K 190       200       210       220       230       240
          |         |         |         |         |         |
TCACCGACTATCTTAAAAGTTCGACAACAGAGTCCAAGAAAATACGTTACGTTTCCATTG
 S  P  T  I  L  K  V  R  Q  Q  S  P  R  K  Y  V  T  F  P  L 250       260       270       280       290       300
          |         |         |         |         |         |
GTTTTGAATAATACAGTGAGTGCTATTGTGAAGAGGCCAAAGAAATCAAGGAGCAAGAAA
 V  L  N  N  T  V  S  A  I  V  K  R  P  K  K  S  R  S  K  K 310       320       330       340       350       360
          |         |         |         |         |         |
GAGAAGGAAGAAGAGGAAGAGGTTTTAGTGATTGAGGGGATTGAGTTTGATATGAATATA
 E  K  E  E  E  E  E  V  L  V  I  E  G  I  E  F  D  M  N  I 370       380       390       400       410       420
          |         |         |         |         |         |
GCCATTAAGTTTGATGTTTATATTAATGATGAAGATGCTAAGGTTGGGCCAGGGAATACT
 A  I  K  F  D  V  Y  I  N  D  E  D  A  K  V  G  P  G  N  T
```

FIGURE 2-2

```
         430       440       450       460       470       480
          |         |         |         |         |         |
GAGTTTGCTGGAAGCTTTGTGAATGTCCCTCATTCCTCACATGGACACAGTAACAAGATT
 E  F  A  G  S  F  V  N  V  P  H  S  S  H  G  H  S  N  K  I 490       500       510       520       530       540
          |         |         |         |         |         |
ATTACTTGTTTAAGACTTGGTATAACTGATTTGTTGGAAGATTTGGATGTCGAAGGCGAT
 I  T  C  L  R  L  G  I  T  D  L  L  E  D  L  D  V  E  G  D 550       560       570       580       590       600
          |         |         |         |         |         |
GATAATATTGTGGTTACATTGGTTCCAAAATGTGGGAATGGACAAGTCAAAATCAATAAC
 D  N  I  V  V  T  L  V  P  K  C  G  N  G  Q  V  K  I  N  N 610       620       630       640       650       660
          |         |         |         |         |         |
GTCGAGATAGTGTTTGAAGATTGAAAATTTCTACCACTTTGTTATGCACCGTCTGTGTTG
 V  E  I  V  F  E  D  -

670       680       690
          |         |         |
AGCGACTTGAGAGGTAGATTTTATGTTTTTT
```

FIGURE 3 pSR7

```
         10        20        30        40        50        60
          |         |         |         |         |         |
GAGGACATGGGGAACTTTTACTCCGCCGGTCGGGATCCCCTGTTTTACGCCCACCATTGC
  E  D  M  G  N  F  Y  S  A  G  R  D  P  L  F  Y  A  H  H  C 70        80        90       100       110       120
          |         |         |         |         |         |
AACGTGGACCGCATGTGGAACGTTTGGAAAACCCTCGGAGGCAAGCGCAAGGACCCCACC
  N  V  D  R  M  W  N  V  W  K  T  L  G  G  K  R  K  D  P  T 130       140       150       160       170       180
          |         |         |         |         |         |
GACACCGATTGGCTTGACGCTGAGTTTCTGTTCTACGATGAAAACGCCGAGCTTGTGAGC
  D  T  D  W  L  D  A  E  F  L  F  Y  D  E  N  A  E  L  V  S 190       200
          |         |
TGTAAAGTTCGGGACAGCCTCAAC
  C  K  V  R  D  S  L  N
``` pSR8

```
         10        20        30        40        50        60
          |         |         |         |         |         |
GAGGATATGGGGAATTTTTACTCTGCGGGGAGGGATCCGCTGTTTTACTCTCACCATTCC
  E  D  M  G  N  F  Y  S  A  G  R  D  P  L  F  Y  S  H  H  S 70        80        90       100       110       120
          |         |         |         |         |         |
AACGTGGACCGCATGTGGTCTATATATAAAGATAAGTTGGGAGGTACGGACATAGAAAAA
  N  V  D  R  M  W  S  I  Y  K  D  K  L  G  G  T  D  I  E  K 130       140       150       160       170
          |         |         |         |         |
TACCGACTGCTGGACGCAGAGTTCTTATTCTACGACGAGAACAAGAATCTTCGTGC
  Y  R  L  L  D  A  E  F  L  F  Y  D  E  N  K  N  L  R
```

FIGURE 4-1 pSRP32

```
         10         20         30         40         50         60
          |          |          |          |          |          |
TTTTTGCCGTTTCATCGATGGTACTTGTACTTCCACGAGAGAATCGTGGGAAAATTCATT
  F  L  P  F  H  R  W  Y  L  Y  F  H  E  R  I  V  G  K  F  I 70         80         90        100        110        120
          |          |          |          |          |          |
GATGATCCAACTTTCGCTTTACCATATTGGAATTGGGACCATCCAAAAGGTATGCGTTTT
  D  D  P  T  F  A  L  P  Y  W  N  W  D  H  P  K  G  M  R  F 130        140        150        160        170        180
          |          |          |          |          |          |
CCTGCCATGTATGATCGTGAAGGGACTTCCCTTTTCGATGTAACACGTGACCAAAGTCAC
  P  A  M  Y  D  R  E  G  T  S  L  F  D  V  T  R  D  Q  S  H 190        200        210        220        230        240
          |          |          |          |          |          |
CGAAATGGAGCAGTAATCGATCTTGGTTTTTTCGGCAATGAAGTTGAAACAACTCAACTC
  R  N  G  A  V  I  D  L  G  F  F  G  N  E  V  E  T  T  Q  L 250        260        270        280        290        300
          |          |          |          |          |          |
CAGTTGATGAGCAATAATTTAACACTAATGTACCGTCAAATGGTAACTAATGCTCCATGT
  Q  L  M  S  N  N  L  T  L  M  Y  R  Q  M  V  T  N  A  P  C 310        320        330        340        350        360
          |          |          |          |          |          |
CCTCGGATGTTCTTTGGCGGGCCTTATGATCTCGGGGTTAACACTGAACTCCCGGGAACT
  P  R  M  F  F  G  G  P  Y  D  L  G  V  N  T  E  L  P  G  T 370        380        390        400        410        420
          |          |          |          |          |          |
ATAGAAAACATCCCTCACGGTCCTGTCCACATCTGGTCTGGTACAGTGAGAGGTTCAACT
  I  E  N  I  P  H  G  P  V  H  I  W  S  G  T  V  R  G  S  T 430        440        450        460        470        480
          |          |          |          |          |          |
TTGCCCAATGGTGCAATATCAAACGGTGAGAATATGGGTCATTTTTACTCAGCTGGTTTG
  L  P  N  G  A  I  S  N  G  E  N  M  G  H  F  Y  S  A  G  L 490        500        510        520        530        540
          |          |          |          |          |          |
GACCCGGTTTTCTTTTGCCATCACAGCAATGTGGATCGGATGTGGAGCGAATGGAAAGCG
  D  P  V  F  F  C  H  H  S  N  V  D  R  M  W  S  E  W  K  A
```

FIGURE 4-2

```
          550        560        570        580        590        600
           |          |          |          |          |          |
ACAGGAGGGAAAAGAACGGATATCACACATAAAGATTGGTTGAACTCCGAGTTCTTTTTC
 T  G  G  K  R  T  D  I  T  H  K  D  W  L  N  S  E  F  F  F 610        620        630        640        650        660
           |          |          |          |          |          |
TATGATGAAAATGAAAACCCTTACCGTGTGAAAGTCAGAGACTGTTTGGACACGAAGAAG
 Y  D  E  N  E  N  P  Y  R  V  K  V  R  D  C  L  D  T  K  K 670        680        690        700        710        720
           |          |          |          |          |          |
ATGGGATACGATTACAAACCAATTGCCACACCATGGCGTAACTTCAAGCCCTTAACAAAG
 M  G  Y  D  Y  K  P  I  A  T  P  W  R  N  F  K  P  L  T  K 730        740        750        760        770        780
           |          |          |          |          |          |
CCTTCAGCTGGAAAAGTGAATACAGCTTCACTTCCGCCAGCTAGCAATGTATTCCCATTG
 P  S  A  G  K  V  N  T  A  S  L  P  P  A  S  N  V  F  P  L 790        800        810        820        830        840
           |          |          |          |          |          |
GCTAAACTCGACAAAGCAATTTCGTTTTCCATCAATAGGCCGACTTCGTCAAGGACTCAA
 A  K  L  D  K  A  I  S  F  S  I  N  R  P  T  S  S  R  T  Q 850        860        870        880        890        900
           |          |          |          |          |          |
CAAGAGAAAAATGCACAAGAGGAGATGTTGACATTCAGTAGCATAAGATATGATAACAGA
 Q  E  K  N  A  Q  E  E  M  L  T  F  S  S  I  R  Y  D  N  R 910        920        930        940        950        960
           |          |          |          |          |          |
GGGTACATAAGGTTCGATGTGTTTTCGAACGTGGACAATAATGTGAATGCGAATGAGCTT
 G  Y  I  R  F  D  V  F  S  N  V  D  N  N  V  N  A  N  E  L 970        980        990       1000       1010       1020
           |          |          |          |          |          |
GACAAGGCGGAGTTTGCGGGGAGTTATACAAGTTTGCCACATGTTCATAGAGCTGGTGAG
 D  K  A  E  F  A  G  S  Y  T  S  L  P  H  V  H  R  A  G  E 1030       1040       1050       1060       1070       1080
           |          |          |          |          |          |
ACTAATCATATCGCGACTGTTGATTTCCAGCTGGCGATAACGGAACTGTTGGAGGATATT
 T  N  H  I  A  T  V  D  F  Q  L  A  I  T  E  L  L  E  D  I
```

FIGURE 4-3

```
          1090      1100      1110      1120      1130      1140
            |         |         |         |         |         |
         GGTTTGGAAGATGAAGATACTATTGCGGTGACTCTGGTGCCAAAGAGAGGTGGTGAAGGT
          G  L  E  D  E  D  T  I  A  V  T  L  V  P  K  R  G  G  E  G 1150      1160      1170      1180      1190      1200
            |         |         |         |         |         |
         ATCTCCATTGAAGGTGCGACGATCAGTCTTGCAGATTGTTAATTAGTCTCTATTGAATCT
          I  S  I  E  G  A  T  I  S  L  A  D  C  -  L  V  S  I  E  S 1210      1220      1230      1240      1250      1260
            |         |         |         |         |         |
         GCTGAGATTACACTTTGATGGATGATGCTCTGTTTTTGTTTTCTTGTTCTGTTTTTTCCT
          A  E  I  T  L  -  W  M  M  L  C  F  C  F  L  V  L  F  F  P 1270      1280      1290      1300      1310      1320
            |         |         |         |         |         |
         CTGTTGAAATCAGCTTTGTTGCTTGATTTCATTGAAGTTGTTATTCAAGAATAAATCAGT
          L  L  K  S  A  L  L  L  D  F  I  E  V  V  I  Q  E  -  I  S

TACAA
          Y
```

FIGURE 4-4 pSRP33

```
          10         20         30         40         50         60
           |          |          |          |          |          |
TTCTTGCCGTTCCACCGATGGTACTTATACTTCTACGAGAGAATATTGGGAAAACTCATC
 F  L  P  F  H  R  W  Y  L  Y  F  Y  E  R  I  L  G  K  L  I 70         80         90        100        110        120
           |          |          |          |          |          |
GATGATCCAACTTTCGCTTTACCATATTGGAATTGGGATCATCCAAAGGGCATGCGTTTA
 D  D  P  T  F  A  L  P  Y  W  N  W  D  H  P  K  G  M  R  L 130        140        150        160        170        180
           |          |          |          |          |          |
CCTCCCATGTTCGATCGTGAAGGAACTTCTATTTACGACGAAAGGCGTAATCAACAAGTC
 P  P  M  F  D  R  E  G  T  S  I  Y  D  E  R  R  N  Q  Q  V 190        200        210        220        230        240
           |          |          |          |          |          |
CGTAACGGAACCGTTATGGATCTTGGTTCATTTGGGGACAAGGTCCAAACAACTCAACTC
 R  N  G  T  V  M  D  L  G  S  F  G  D  K  V  Q  T  T  Q  L 250        260        270        280        290        300
           |          |          |          |          |          |
CAGTTGATGAGCAATAATTTAACACTAATGTACCGTCAAATGGTAACTAATGCTCCATGT
 Q  L  M  S  N  N  L  T  L  M  Y  R  Q  M  V  T  N  A  P  C 310        320        330        340        350        360
           |          |          |          |          |          |
CCTCTTTTGTTCTTCGGTGCGCCTTACGTTCTTGGGAATAACGTCGAAGCCCCGGGAACC
 P  L  L  F  F  G  A  P  Y  V  L  G  N  N  V  E  A  P  G  T 370        380        390        400        410        420
           |          |          |          |          |          |
ATTGAAAACATCCCTCATATACCTGTCCATATTTGGGCTGGTACAGTACGTGGTTCAACA
 I  E  N  I  P  H  I  P  V  H  I  W  A  G  T  V  R  G  S  T 430        440        450        460        470        480
           |          |          |          |          |          |
TTTCCTAATGGTGATACGTCATACGGTGAGGATATGGGTAATTTCTACTCAGCTGGTTTA
 F  P  N  G  D  T  S  Y  G  E  D  M  G  N  F  Y  S  A  G  L 490        500        510        520        530        540
           |          |          |          |          |          |
GACCCGGTTTTCTATTGCCACCACGGCAATGTGGACCGTATGTGGAATGAATGGAAGGCA
 D  P  V  F  Y  C  H  H  G  N  V  D  R  M  W  N  E  W  K  A
```

FIGURE 4-5

```
         550       560       570       580       590       600
          |         |         |         |         |         |
ATAGGAGGTAAGAGAAGGGATTTATCAGAAAAAGATTGGTTGAACTCTGAGTTCTTCTTT
 I  G  G  K  R  R  D  L  S  E  K  D  W  L  N  S  E  F  F  F 610       620       630       640       650       660
          |         |         |         |         |         |
TATGATGAAAACAAAAAGCCTTACCGTGTGAAAGTCCGAGACTGTTTGGACGCGAAGAAA
 Y  D  E  N  K  K  P  Y  R  V  K  V  R  D  C  L  D  A  K  K 670       680       690       700       710       720
          |         |         |         |         |         |
ATGGGGTACGATTACGCACCAATGCCAACTCCATGGCGTAACTTCAAACCAAAAACAAAG
 M  G  Y  D  Y  A  P  M  P  T  P  W  R  N  F  K  P  K  T  K 730       740       750       760       770       780
          |         |         |         |         |         |
GCATCAGTAGGGAAAGTGAATACAACTACACTCCCCCCAGTGAACAAGGTATTCCCACTC
 A  S  V  G  K  V  N  T  T  T  L  P  P  V  N  K  V  F  P  L 790       800       810       820       830       840
          |         |         |         |         |         |
ACGAAGATGGATAAAGCCATTTCATTTTCCATCAATAGGCCTGCTTCATCGCGGACTCAA
 T  K  M  D  K  A  I  S  F  S  I  N  R  P  A  S  S  R  T  Q 850       860       870       880       890       900
          |         |         |         |         |         |
CAAGAGAAAAATGAACAAGAGGAGATGTTAACGTTCGATAACATAAAATATGATAATAGA
 Q  E  K  N  E  Q  E  E  M  L  T  F  D  N  I  K  Y  D  N  R 910       920       930       940       950       960
          |         |         |         |         |         |
GGGTATATAAGGTTCGATGTATTTCTGAACGTGGATAACAATGTGAATGCGAATGAGCTT
 G  Y  I  R  F  D  V  F  L  N  V  D  N  N  V  N  A  N  E  L 970       980       990      1000      1010      1020
          |         |         |         |         |         |
GATAAGGCAGAGTTCGCGGGGAGTTATACTAGTTTGCCACATGTTCACAGAGTTGGCGAG
 D  K  A  E  F  A  G  S  Y  T  S  L  P  H  V  H  R  V  G  E 1030      1040      1050      1060      1070      1080
          |         |         |         |         |         |
AATGATCATACCGCGACTGTTACTTTCCAGCTGGCGATAACAGAACTGTTGGAGGACATT
 N  D  H  T  A  T  V  T  F  Q  L  A  I  T  E  L  L  E  D  I
```

FIGURE 4-6

```
            1090       1100       1110       1120       1130       1140
              |          |          |          |          |          |
     GGTTTGGAAGATGAAGAGACTATTGCGGTGACTCTGGTACCAAAGAAAGGTGGTGAAGGT
       G  L  E  D  E  E  T  I  A  V  T  L  V  P  K  K  G  G  E  G 1150       1160       1170       1180       1190       1200
              |          |          |          |          |          |
     ATCTCCATTGAAAATGTGGAGATCAAGCTTCTGGATTGTTAAGTACGTTCTCAATTGAAT
       I  S  I  E  N  V  E  I  K  L  L  D  C  -  V  R  S  Q  L  N 1210       1220       1230       1240       1250       1260
              |          |          |          |          |          |
     CTGCTGAGATTACAACTTTGATATGTTTTTTACTTTTGTTTTTCCATGTAACTTTTCCTG
       L  L  R  L  Q  L  -  Y  V  F  Y  F  C  F  S  M  -  L  F  L 1270       1280       1290       1300       1310
              |          |          |          |          |
     TTGAAATCAGCTTGATGCTTGATTTCCTTGGAGTTGTTATTCACTAATAAAATCA
       L  K  S  A  -  C  L  I  S  L  E  L  L  F  T  N  K  I
```

FIGURE 4-7 pID5RACE4

```
         10        20        30        40        50        60
          |         |         |         |         |         |
TTTTTTTTTATTCAAAAGCTAGCAATAATGGCAAGCTTGTGCAATAGTTGTAGTACATCC
                              M  A  S  L  C  N  S  C  S  T  S 70        80        90       100       110       120
          |         |         |         |         |         |
CTCAAAACTCCTTTTACTTCTTCCTCCACTTCTTTAACTTCCACTCCTAAACCCTCTCAA
 L  K  T  P  F  T  S  S  S  T  S  L  T  S  T  P  K  P  S  Q 130       140       150       160       170       180
          |         |         |         |         |         |
CTTTTCATCCATGGAAAACGTAACCAAATGTTCAAAGTTTCATGCATGGTTACCAATAAT
 L  F  I  H  G  K  R  N  Q  M  F  K  V  S  C  M  V  T  N  N 190       200       210       220       230       240
          |         |         |         |         |         |
AACGGTGACCAAAACCAAAACGTTGAAACGAATTCTGTTGATCGAAGAAATGTTCTTCTT
 N  G  D  Q  N  Q  N  V  E  T  N  S  V  D  R  R  N  V  L  L 250       260       270       280       290       300
          |         |         |         |         |         |
GGCTTAGGTGGTCTTTATGGTGTTGCTAATGCTATACCATTAGCTGCATCCGCTACTCCA
 G  L  G  G  L  Y  G  V  A  N  A  I  P  L  A  A  S  A  T  P 310       320       330       340       350       360
          |         |         |         |         |         |
TCTCCACCTCCTGATCTCTCGTCTTGTAGTATAGCCAGGATTAACGAAACTCATGTGGTG
 S  P  P  P  D  L  S  S  C  S  I  A  R  I  N  E  T  H  V  V 370       380       390       400       410       420
          |         |         |         |         |         |
CCGTACAGTTGTTGCGCGCCTAAGCCTGATGATATGGAGAAAGTTCCGTATTACAAGTTC
 P  Y  S  C  C  A  P  K  P  D  D  M  E  K  V  P  Y  Y  K  F 430       440       450       460       470       480
          |         |         |         |         |         |
CCTTCTATGACTAAGCTCCGTGTTCGTCAGCCTGCTCATGAAGCTAATGAGGAGTATATT
 P  S  M  T  K  L  R  V  R  Q  P  A  H  E  A  N  E  E  Y  I 490       500       510       520       530       540
          |         |         |         |         |         |
GCCAAGTACAATTTGGCGGTTAGCAAGATGAGGGATCTTGATAAGACACAACCTTTAAAC
 A  K  Y  N  L  A  V  S  K  M  R  D  L  D  K  T  Q  P  L  N
```

FIGURE 4-8

```
         550        560        570        580        590        600
          |          |          |          |          |          |
CCTATTGGTTTTAAGCAACAAGCTAATATACATTGTGCTTATTGTAACGGTGCTTATAGA
 P  I  G  F  K  Q  Q  A  N  I  H  C  A  Y  C  N  G  A  Y  R 610        620        630        640        650        660
          |          |          |          |          |          |
ATTGGTGGCAAAGAGTTACAAGTTCATAATTCTTGGCTTTTCTTCCCGTTCCATAGATGG
 I  G  G  K  E  L  Q  V  H  N  S  W  L  F  F  P  F  H  R  W 670        680        690        700        710        720
          |          |          |          |          |          |
TACTTGTACTTCTACGAGAGAATCGTGGGAAAATTCATTGATGATGCAACTTTCGCTTTG
 Y  L  Y  F  Y  E  R  I  V  G  K  F  I  D  D  A  T  F  A  L 730        740        750        760        770        780
          |          |          |          |          |          |
CCATATTGGAATTGGGACCATCCAAAGGGTATGCGTTTTCCTGCCATGTATGATCGTGAA
 P  Y  W  N  W  D  H  P  K  G  M  R  F  P  A  M  Y  D  R  E 790        800        810        820        830        840
          |          |          |          |          |          |
GGGACTTCCCTTTTCGATGTAACACGTGACCAAAGTCACCGAAATGGAGCAGTAATCGAT
 G  T  S  L  F  D  V  T  R  D  Q  S  H  R  N  G  A  V  I  D 850        860        870        880        890
          |          |          |          |          |
CTTGGTTTTATCGGCAATGAAGTCGAAACAACTCAACTCCAGTTGATGAGCA
 L  G  F  I  G  N  E  V  E  T  T  Q  L  Q  L  M  S
```

POLYPHENOL OXIDASE GENES

This is a divisional of application Ser. No. 08/182,045, filed Feb. 14, 1994 which is 371 of PCT/AU92/00356 filed Jul. 16, 1992, which application is incorporated herein by reference.

The present invention relates to a method of modifying polyphenol oxidase (PPO) activity in fruit and vegetables and to DNA sequences for use therein.

Browning of plant tissues often occurs following injury or damage and this generally results in spoilage of fruit and vegetables. Undesirable browning also occurs during processing of plant materials to produce food or other products. Steps are taken during transport, storage, and processing to prevent these browning reactions. Often this involves the use of chemicals such as sulphur dioxide but the use of these substances is likely to be restricted in the future due to concerns about their safety and consumer acceptance. For example, the US Food and Drug Administration banned the use of sulphite for most fresh fruit and vegetables in 1986. The production of fruit and vegetable varieties with an inherently low susceptibility to brown would remove the need for these chemical treatments.

Accordingly, it is an object of the present invention to overcome or at least alleviate one or more of the difficulties related to the prior art.

It will be understood that browning in plants is predominantly catalysed by the enzyme PPO. PPO is localised in the plastids of plant cells whereas the phenolic substrates of the enzyme are stored in the plant cell vacuole. This compartmentation prevents the browning reaction from occurring unless the plant cells are damaged and the enzyme and its substrates are mixed. If the amount of this enzyme could be decreased the susceptibility of the tissue to brown would be reduced.

PPO sequence information may be used to construct synthetic genes which genes may be transformed into plants to decrease expression of the normal PPO gene, thereby decreasing synthesis of the enzyme.

It will also be understood that in certain instances the browning reactions in plants are desirable, such as in the production of black tea, cocoa, coffee, black pepper, black olives, etc. In these instances it may be desirable to increase the level of PPO to produce desired levels of browning or changes in flavour compounds.

The role of PPO in normal plant growth and development is not understood at present. There are a number of instances where increased levels of this enzyme are correlated with increased resistance to plant pathogens. It follow that genetic manipulation of plants to increase the level of PPO activity may confer useful resistance against pathogens and pests.

The grapevine PPO gene codes for an additional 103 amino acids upstream of the N-terminus of the mature protein. This region has the properties of a chloroplast transit peptide and is most likely responsible for targeting of the protein to be imported into the chloroplast and processed to produce the mature PPO protein. Transformation of plants with this gene may therefore result in correct targeting and maturation of the grapevine PPO in other species and result in accumulation of active grapevine PPO enzyme in the plastids of these tissues.

The terms "gene encoding PPO", "gene coding for PPO" or "PPO gene" as used herein should be understood to refer to the PPO gene or a sequence substantially homologous therewith.

In a first aspect of the present invention, there is provided a DNA sequence including a gene coding for a polypeptide having plant polyphenol oxidase (PPO) activity or a fragment thereof.

The DNA sequence may include a pre-sequence of a plant PPO gene coding for a transit peptide.

The DNA sequence may be modified. The DNA sequence may include a sequence coding for antisense mRNA to a plant PPO gene, or a fragment thereof.

The DNA sequence may include a catalytic cleavage site.

Alternatively the presequence may be replaced by other targeting sequences to direct the polypeptide having plant PPO activity to other cellular compartments.

The DNA sequence may include a putative chloroplast transit sequence and a mature grape vine PPO protein, as illustrated in FIG. 1.

The DNA sequence may include a gene coding for a polypeptide having a broad bean leaf PPO activity, as illustrated in FIG. 2.

The DNA sequence may include a gene coding for a polypeptide having apple fruit PPO activity, as illustrated in FIG. 3.

The DNA sequence may include a gene coding for a polypeptide having potato tuber PPO activity, as illustrated in FIG. 4.

In a further aspect of the present invention there is provided a DNA sequence including a sequence coding for antisense mRNA to a plant PPO gene, or a fragment thereof.

In a further aspect of the present invention there is provided a method for preparing a recombinant DNA plasmid including a DNA sequence coding for a polypeptide having plant PPO activity or a fragment thereof, which method includes providing
   a DNA sequence including a gene coding for a polypeptide having PPO activity or a fragment thereof; and
   a plasmid expression vector; and
reacting the DNA sequence and the plasmid expression vector to deploy the DNA sequence within the plasmid expression vector.

The DNA sequence coding for PPO may be formed from polyadenylated RNA, for example isolated from a plant sample. The plant may be selected from apples, potatoes, grapes and beans. Preferably the plant sample is isolated from sultana grape berries, broad bean leaves, apple peel or cortex or potato tubers.

In order to provide a DNA sequence coding for PPO, in a preferred aspect of the present invention the method for the preparation of a recombinant DNA plasmid may include the preliminary steps of providing a source of a polypeptide having plant PPO activity;
isolating polyadenylated RNA coding for a polypeptide having plant PPO activity therefrom; and
treating the polyadenylated RNA to construct copy DNA (cDNA).

The isolation of the polyadenylated RNA may be conducted utilising an oligo-dT spun column.

The step of treating the polyadenylated RNA to construct cDNA according to this aspect of the present invention may include treating the polyadenylated RNA with reverse transcriptase and an adapter primer to form first strand cDNA; and
amplifying the cDNA so formed using the polymerase chain reaction (PCR).

The step of reacting the polyadenylated RNA with reverse transcriptase may utilise an oligonucleotide adapter primer having the sequence

5'-GACTCGAGTCGACATCGATTTTTTTTTTTTTT
TT(SEQ ID NO: 15)

The step of amplifying the cDNA may utilise an adapter primer having the sequence 5'-GACTCGAGTCGACATCG(SEQ ID NO: 16) and a 5'-end primer.

The 5'-end primer may have the sequence

5'-CCIATICAGGCICCIGATATIICIAAGTGTGG(SEQ ID NO: 17) when utilized for the amplification of grape cDNA.

The 5'-end primer may have the sequence

5'-GCGGATCCTT[CT]TA[CT]GA[CT]GA[GA]AA[CT]AA(SEQ ID NO: 18).

when utilized for the amplification of bean cDNA.

The 5'-end primer may have the sequence

5'-GCGAATTCGA[AG]GA[TC]ATGGGIAA[TC]TT[TC]TA)(SEQ ID NO: 19)

when utilised for the amplification of apple cDNA.

The 5'-end primer may have the sequences

GEN3: (5'-GCGAATTCTT[TC][TC]TICCITT[TC]CA[TC][AC]G)(SEQ ID NO: 20)

GEN7: (5'-GCGAATTCAA[TC]GTIGA[TC][AC]GIATGTGG)(SEQ ID NO: 21)

when utilised for the amplification of potato cDNA.

Alternatively, the step of treating the polyadenylated RNA to construct cDNA according to this aspect of the present invention may include treating the polyadenylated RNA with reverse transcriptase and a PPO specific primer to form first strand cDNA;

treating the cDNA so formed with terminal d Transferase to attach a polyadenosine tail sequence at the 3' end of the cDNA; and amplifying the polyadenylated cDNA so formed by PCR.

The step of treating the polyadenylated RNA with reverse transcriptase may utilise a PPO specific oligonucleotide primer having the sequence

5'-AATCTTTGTGGTGACTGGCG(SEQ ID NO: 22)

for grape PPO or the PPO-specific primer is an oligonucleotide primer having the sequence

5'-GACGGTACATTAGTCTTAAAT(SEQ ID NO: 23)

for potato tuber PPO.

The step of amplifying the cDNA may utilise an oligonucleotide adapter primer having the sequence

5'-GACTCGAGTCGACATCGATTTTTTTTTTTTTT
TT(SEQ ID NO: 15)

and a PPO specific oligonucleotide primer having the sequence

5'-ACCATCAGGCACGGTGGCGG(SEQ ID NO: 24)

for grape PPO or the sequence

5'-TGCTCATCAACTGGAGTTGAG(SEQ ID NO: 25)

for potato tuber PPO.

The plasmid expression vector for the cloning of th double stranded cDNA may be of any suitable type. The plasmid vector Bluescript SK+ has been found to be suitable.

The cloning step may take any suitable form. A preferred form may include blunt-ending the cDNA, for example with Klenow fragment;

fractionating the cDNA so formed, for example on an Agarose gel;

isolating a fragment of the expected size, for example from the gel; and ligating said fragment into a suitable restriction enzyme site, for example the HindIII or EcoRI site of a Bluescript SK+ vector.

In order to test the clones so formed, a suitable microorganism may be transformed with the plasmid expression vector, the microorganism cultured and the polypeptide encoded therein expressed. The microorganism *Escherichia coli* DH5 has been found to be suitable.

In a further aspect of the present invention there is provided a recombinant DNA plasmid including a DNA sequence coding for a polypeptide having plant PPO activity, or a fragment thereof, which plasmid is capable of being replicated, transcribed and translated in a unicellular organism.

The plasmid expression vector may be of any suitable type. The recombinant plasmid may contain a constitutive promoter element upstream of the DNA sequence coding for a polypeptide having PPO activity.

In a further aspect of the present invention there is provided a method of decreasing the level of PPO activity in a plant tissue, which method includes providing a DNA construct including a modified gene coding for a polypeptide having plant PPO activity or fragment thereof; and a plant sample; and introducing said DNA construct into said plant sample to produce a transgenic plant.

The DNA construct may include a sequence encoding antisense mRNA to a plant PPO gene or a fragment thereof. The DNA construct may include a gene coding for a polypeptide having plant PPO activity or fragment thereof incorporating a catalytic cleavage site. X The plant may be of any suitable type. In a preferred aspect the plant may be selected from the group including grapevine, potato, apple and bean.

In a further aspect of the present invention there is provided a method of increasing the level of PPO activity in a plant tissue, which method includes providing a DNA construct including a gene coding for a polypeptide having plant PPO activity or a fragment thereof; and a plant sample; and introducing said DNA construct into said plant sample to produce a transgenic plant.

The DNA construct may include a DNA sequence encoding a pre-sequence of a plant PPO gene or a fragment thereof.

The plant may be of any suitable type. In a preferred aspect the plant may be selected from the group comprising tobacco, broad bean, tomato, tea, coffee and cocoa.

The pre-sequence coding for the transit peptide may be replaced with other targeting sequences to direct the PPO protein to other cellular compartments. Sequences are already known which direct foreign genes into the vacuole, mitochondrion or intercellular space of plant cells. In addition the transit sequence for grapevine PPO could be used to target other proteins into the plastids.

The DNA construct may include a constitutive promoter which would result in expression of the introduced genes throughout the plant.

It will be understood that in many plant tissues PPO is highly expressed in certain tissue types. For example, PPO activity is much higher in the skin of grape berries than in the pulp, and the peel of potato tubers has higher activity than the cortex.

It may be desirable to alter levels of PPO activity only in certain plant tissues or at certain stages of plant development and this may be achieved by the use of specific promoter elements. For example, use of the patatin promoter alters PPO levels only in the tuber tissue of potato plants. This decreases PPO activity in the tuber, and reduce browning, but PPO activity in other parts of the potato plant is not altered.

Accordingly, the DNA construct may include a promoter which is specific to the peel or skin of fruit and vegetables to target foreign proteins specifically to the outer tissue layers.

This may allow properties of the skin or peel, such as colour, flavour, resistance to pathogens, etc to be manipulated independently of the inner parts of the fruit or vegetable which are consumed.

In a preferred aspect, the DNA construct may include a binary vector into which has been introduced a DNA sequence encoding PPO or a fragment thereof.

In a further preferred aspect, the introduction of the DNA construct into the plant may be by infection of the plant with an Agrobacterium containing the DNA construct.

In a further aspect of the present invention there is provided a transgenic plant, which plant contains a synthetic gene capable of modifying expression of the normal PPO gene.

The plant may be of any suitable type. In a preferred aspect the plant may be selected from the group comprising grapevine, potato, apple, tobacco, bean, peach, pear and apricot.

In a still further aspect of the present invention there is provided a plant vaccine including a sequence encoding PPO or a fragment thereof.

In a still further aspect of the present invention there is provided a DNA probe including a DNA sequence coding for a polypeptide having plant PPO activity or a fragment thereof.

The probe may be labelled in any suitable manner. A radioactive or non-radioactive labelling may be used. For convenience, the probe may be provided in the form of a cloned insert in a suitable plasmid vector.

The grapevine PPO sequence may be used to design general purpose oligonucleotide primers for use in the PCR to obtain this gene from other species. Plant PPO proteins are known to contain copper as a prosthetic group and two regions of the grape protein sequence which show homology to sequences from hemocyanin and tyrosinase proteins, corresponding to the copper binding sites on these proteins have been identified. Since these regions are apparently conserved between widely diverse organisms they are suitable for design of probes and primers to obtain other plant PPO genes.

Accordingly, in a still further aspect of the present invention there is provided a method of isolating a DNA sequence including a gene coding for a polypeptide having PPO activity or a fragment thereof from a plant species, which method includes
  providing
    a cDNA or genomic library; and
    a DNA probe including a DNA sequence coding for a polypeptide having plant PPO activity or a fragment thereof; and
  hybridising the probe with the genomic library to identify clones containing said DNA sequence.

The DNA probe may include a DNA sequence including, a fragment of the apple, potato, grape or bean PPO gene which is highly-conserved between different species.

The DNA probe may be prepared by a method which includes
  providing
    total cDNA from a plant species; and
    two or more oligonucleotide primers which hybridise specifically with a gene coding for a polypeptide having plant PPO activity and which include sequences of the apple, potato, grape or bean PPO gene which are highly conserved between different species; and
  performing PCT to amplify a DNA sequence including a gene coding for a polypeptide having plant PPO activity or a fragment thereof.

The oligonucleotide primers may include DNA sequences corresponding to the copper binding sites on the polypeptide having plant PPO activity.

In a still further aspect of the present invention there is provided a method of isolating a DNA sequence including a gene coding for a polypeptide having PPO activity, or a fragment thereof, from a plant species, which method includes
  providing
    mRNA isolated from the plant;
    a poly-dT adapter primer; and
    two or more oligonucleotide primers;
  treating the mRNA with reverse transcriptase and an adapter primer to form first strand cDNA; and
  amplifyig the cDNA so formed using the oligonucleotide primers and the polymerase chain reaction.

In a preferred aspect the oligonucleotide primers may be based on the apple, potato, grape or bean PPO gene sequences.

In a still further aspect of the present invention there is provided a method of isolating a DNA sequence including a gene coding for a polypeptide having PPO activity or a fragment thereof from a plant species, which method includes
  providing
    an expression library; and
    a polyclonal antibody which has been raised against a purified polypeptide having PPO activity; and
  reacting the polyclonal antibody with the expression library to identify clones containing a DNA sequence including a gene coding for a polypeptide having PPO activity or fragments thereof.

In a still further aspect of the present invention there is provided a method for purification of the PPO protein, which method includes
  providing
    a plant sample;
    a detergent; and
    one or more chromatography columns;
  extracting the plant sample with the detergent;
  treating the extract so formed with ammonium sulphate; and
  fractionating the extract so formed by passing it through the chromatography columns.

The plant sample may be of any suitable type. The plant sample may be grapevine berries. This tissue contains high levels of PPO and in the juice of mature grape berries most of the PPO activity is bound to the solids and can be separated from the juice by centrifugation and then solubilised with detergents. The plant sample may be bean leaves.

The detergent may be cationic. The detergent hexadecyltrimethylammonium bromide (CTAB) has been found to be suitable.

The chromatography columns may be sepharose based. Three chromatography columns may be used. Q-sepharose followed by phenyl-sepharose followed by hydroxylapatite has been found to be suitable.

In a further aspect of the present invention there substantially pure form, having the N-terminal amino acid sequence

APIQAPDISKCGTATVPDGVTP(SEQ ID NO: 26)

The present invention will now be more fully described with reference to the accompanying Examples and drawings. It should be understood, however, that the description following is illustrative only and should not be taken in any way as a restriction on the generality of the invention described above.

In the figures:

FIG. 1:

The composite full-length GPO1 cDNA nucleotide sequence and derived protein sequence encoding both the putative chloroplast transit sequence and the mature grapevine PPO-protein.

The translation start site is shown in bold face and the N-terminal of the mature PPO protein is marked with an asterisk. The dashed line indicates the location of the N-terminal primer and the two solid lines indicate the regions used to construct the two antisense primers for cloning the transit peptide sequence.

FIGS. 2–1 and 2–2:

Nucleic acid (SEQ ID NO: 3) and derived protein sequence (SEQ ID NO: 4) of the BPO1 clone of broad bean leaf polyphenol ozidase. The solid line indicates the region of the B15 primer used to amplify the cDNA by the polymerase chain reaction.

FIG. 3:

Nucleic acid and derived protein sequences of the clones pSR7 (SEQ ID NO:5 and 6, respectively) and pSR8 (SEQ ID NO:7 and 8, respectively) encoding apple fruit PPO. The solid line indicates the region of the GEN4 primer used to amplify the cDNA by the polymerase chain reaction.

FIGS. 4–1 to 4–8:

Nucleic acid (SEQ ID NO: 13) and derived protein sequences (SEQ ID NO: 14) of the clones encoding potato tuber PPO. The solid line indicates the region of the GEN3 primer used to amplify the cDNA by the polymerase chain reaction.

EXAMPLE 1

Purification of the PPO Protein

PPO was purified from grapevine berries. Initial experiments showed that this tissue contained high levels of the enzyme and that there appeared to be only one form of the enzyme as determined by electrophoresis in sodium dodecyl sulphate polyacrylamide (SDS-PAGE) gels. In the juice of mature grape berries most of the PPO activity was bound to the solids and could be separated from the juice by centrifugation and then solubilised with detergents. Enzyme activity during the purification was measured as oxygen uptake in the presence of the substrate 4-methyl catechol. All steps during the purification were carried out at 4° C.

Thirty kilograms of Sultana grapes were crushed with a small scale wine press and 100 ml of a solution of 100 mM ascorbate plus 10 mM dithiothreitol was added to each 900 ml of grape juice. The juice was centrifuged for 10 mins at 10,000×g and the supernatant discarded. The pellet fraction was resuspended in 25 mM sodium phosphate, pH 7.2 plus 10 mM ascorbate and 1 mM dithiothreitol to a final volume of 1.75L, then 250 ml of a 4% (w/v) solution of the cationic detergent hezadecyltrimethylammonium bromide (CTAB) was added. After incubating for 20 mins the extract was centrifuged for 15 mins at 15,000×g. The supernatant was brought to 45% saturation with solid ammonium sulphate and the pH was adjusted to 7.0 then it was centrifuged for 15 mins at 15,000×g. This supernatant was brought to 95% saturation with solid ammonium sulphate and the pH was adjusted to 7.0 then it was centrifuged for 30 mins at 15,000×g. The pellet was resuspended in 20 mM Bis-tris-propane, pH 7.5 plus 10 mM ascorbate and 2 mM dithiothreitol (Buffer A) in a final volume of 100 ml. The extract was desalted on a 4×40 cm column of Sephadex G25 equilibrated with Buffer A at a flow rate of 10 ml/min and the active fractions were pooled.

The extract was applied to a 2.5×10 cm column of Q-Sepharose Fast Flow equilibrated with Buffer A at a flow rate of 6 ml/min and then the column was washed with 400 ml of Buffer A. The PPO was eluted with a gradient of 0–500 mM NaCl in Buffer A and the active fractions were pooled. Ammonium sulphate was added to a final concentration of 1M, and the pH was adjusted to 7.0. This fraction was loaded onto a 1×35 cm column of Phenyl Sepharose Fast Flow equilibrated with 50 mM sodium phosphate, pH7.0, plus 1M ammonium sulphate, 1M KCl, and 1 mM dithiothreitol (Buffer B) at a flow rate of 1.5 ml/min. The column was washed with 120 ml Buffer B then the PPO was eluted with a gradient of 100–0% Buffer B. The active fractions were pooled and concentrated on an Amicon PM10 ultrafiltration membrane then diafiltered with the same membrane against three changes of 20 mM potassium phosphate, pH7.0, plus 1 mM dithiothreitol (Buffer C). This fraction was applied to a 1×30 cm column of Hydroxylapatite equilibrated with Buffer C at a flow rate of 1 ml/min. The column was washed with 50 ml of Buffer C then PPO was eluted with a gradient of 0–500 mM potassium phosphate in Buffer C. The pooled active fractions were made 20% (v/v) in glycerol and frozen at −80° C.

This procedure resulted in a 180-fold purification of PPO and yielded 3.5 mg of purified PPO protein. The purification is summarised below:

| Step | Protein (mg) | Act. (U) | Spec.Act. (U/mg) | Recov. (%) | Purif. (-fold) |
|---|---|---|---|---|---|
| Juice* | 19,360 | 7,040 | 0.4 | 100 | 1 |
| CTAB extract | 960 | 2,070 | 2.2 | 29 | 6 |
| Ammonium sulphate | 600 | 1,760 | 2.9 | 25 | 8 |
| Q-Sepharose | 130 | 1,520 | 11.8 | 22 | 33 |
| Phenyl Sepharose | 10.8 | 400 | 37 | 6 | 103 |
| Hydroxylapatite | 3.5 | 230 | 65 | 3 | 180 |

PURIFICATION OF GRAPE BERRY PPO

*From 30 Kg grapes

The purity of the preparation was checked by denaturing SDS-PAGE. A single diffuse band of protein with an apparent molecular weight of 40 kDa was present in the final preparation.

EXAMPLE 2

Amino Acid Sequencing

Approximately 1 mg of purified PPO protein was desalted on a 2.5×20 cm column of Sephadex G25 equilibrated with 20 mM ammonium bicarbonate, pH7.6, at a flow rate of 5 ml/min. The protein peak was collected and dried under nitrogen. The dried protein was carboxymethylated and the N-terminal amino acid sequence was determined with an automated amino acid sequenator by Edman degradation. The following sequence was obtained:

APIQAPDISKCGTATVPDGVTP(SEQ ID NO: 26)

EXAMPLE 3

Cloning of Grape PPO Gene

Total RNA was isolated from Sultana grape berries according to the method of Rezaian and Krake (1). A poly(A)+-enriched RNA fraction was obtained by passing the total RNA through one oligo-dT spun column (Pharmacia LKB Biotechnology).

First strand cDNA was synthesised in a reaction mixture containing 50 mM Tris-HCl pH 8.3, 25 mM KCl, 10 mM $MgCl_2$, 4 mM DTT, 1 mM NaPPi, 1 mM dNTPs, 1 U ribonuclease inhibitor, 1.4 μg grape berry poly(A)+-enriched RNA, 21 U AMV reverse transcriptase (Promega Corp) and 0.5 μg Hybrid dT17-adapter primer (5'-GACTCGAGTCGACATCGATTTTTTTTTTTTT TTT(SEQ ID NO: 15) at 42° C. for 1 h. The reaction mixture was then diluted to 800 μl with TE (10 mM Tris-HCl pH 8.0, 1 mM EDTA) and stored at −20° C. A 32-mer oligonucleotide primer (5'-CCIATICAGGCICCIGATATIICIAAGTGTGG)(SEQ ID NO: 17) was designed to the N-terminal protein sequence (amino acids 2–12) of purified grape PPO. Inosine was utilised in positions in which more than 2 bases could be selected based on codon usage tables. This and all other oligonucleotide primers described were synthesised on an Applied Biosystems DNA synthesiser.

cDNA was amplified by polymerase chain reaction (PCR) essentially according to the method of Frohman (2) in a 50 μl reaction mixture containing 10 mM Tris-HCl (pH 9.0 at 25° C.), 50 mM KCl, 1.5 mM $MgCl_2$, 0.2 mM dNTPs, 0.01% gelatin (w/v), 0.1% Triton X-100, 5 μl diluted 1st. strand cDNA reaction mixture, 1.25 U Tag DNA polymerase (Promega Corp), 100 nM Adapter primer (5'-GACTCGAGTCGACATCG)(SEQ ID NO: 16)

and 1 μM N-terminal primer (described above). Amplification involved an initial program of 5 cycles of denaturation at 94° C. for 1 min, annealing at 55° C. for 1 min, a slow ramp to 72° C. over 2 min and elongation at 72° C. for 3 min followed by 25 cycles of 94° C. for 1 min, 55° C. for 1 min, and 72° C. for 3 min. Amplified DNA was extracted with phenol/chloroform, precipitated with ethanol and resuspended in TE. DNA was blunt-ended with the Klenow fragment and fractionated on a 2% Nusieve GTG agarose (FMC Bioproducts) gel. A 1700 bp fragment was isolated from the gel and ligated into the HincII site of a Bluescript SK+ vector (Stratagene Cloning Systems). Ligated DNA was introduced into *E. coli* DH5. Positive clones (designated GPO) were isolated and sequenced by the dideoxy sequencing method (3).

This confirmed the presence of the N-terminal primer and comparison of the derived protein sequence downstream of the primer with the N-terminal protein sequence obtained for purified grape PPO enzyme above confirmed that this clone coded for grape PPO.

EXAMPLE 4

Cloning the Transit Peptide Sequence

Northern blots of grape mRNA probed with the 1700 bp clone described above identified a transcript of 2200 bp which hybridised with the clone. This suggested that there was further sequence upstream of the 5-prime end of the clone even though the clone did code for the N-terminal of the mature PPO protein. A cDNA clone containing the 5'-end of GPO1 mRNA (encoding the putative transit peptide) was amplified from grape berry RNA essentially as described in (2), but with nested antisense primers. First strand cDNA was synthesised from grape berry poly(A)+-enriched RNA as described above, but with the Hybrid dT17-adapter primer replaced with GPO1-specific primer 1

(5-AATCTTTGTGGTGACTGGCG)(SEQ ID NO: 22)

complementary to a region 44 bases downstream of the N-terminal primer region (i.e. 416–435 nt; FIG. 1). The reaction mixture was diluted to 2 ml with 0.1×TE and centrifuged through a Centricon 30 spin filter (Amicon Corp) at 4000 g for 20 min to remove excess primer. This step was repeated and the remaining liquid concentrated to 20 μl using Speed Vac centrifugation. A poly (dA)-tail sequence was attached at the 3' end of the cDNA strand with Terminal d Transferase (Promega Corp) in a 20 μl reaction mixture containing 11.5 μl cDNA, 4 μl 5×Tailing Buffer (Promega Corp), 4 μl ATP (1 mM) and 10 U Terminal d Transferase incubated at 37° C. for 5 min followed by 65° C. for 5 min and then diluted to 500 μl with TE. PCR amplification of poly(dA)-tailed cDNA was carried out in a reaction mixture containing 10 mM Tris-HCl (pH 9.0 at 25° C.), 50 mM KCl, 1.5 mM $MgCl_2$, 0.2 mM dNTPs, 0.01% gelatin (w/v), 0.1% Triton X-100, 5 μl diluted 1st. strand cDNA reaction mixture, 1.25 U Taq DNA polymerase (Promega Corp), 200 nM Hybrid dT17-adapter primer and 900 nM GPO1-specific primer 2

(5'-ACCATCAGGCACGGTGGCGG)(SEQ ID NO: 24)

complementary to a region immediately downstream to the N-terminal primer binding region (374–393 nt; FIG. 1). Amplification involved 25 cycles of 94° C. for 1 min, 55° C. for 1 min, and 72° C. for 3 min. The resulting 430 bp fragment was cloned into Bluescript SK+ vector, sequenced as described above and found to contain the predicted region of overlapping sequence with the GPO1 clone and confirming this cDNA clone contained the 5' end of the GPO1 mRNA.

EXAMPLE 5

Cloning of the Bean Leaf PPO Gene

Total RNA was isolated from leaves of broad bean according to the method of Rezaian and Krake (1). A poly(A)+-enriched RNA fraction was obtained by passing the total RNA through one oligo-dT spun column (Pharmacia LKB Biotechnology).

First strand cDNA was synthesised in a reaction mixture containing 50 mM Tris-HCl pH 8.3, 25 mM KCl, 10 mM $MgCl_2$, 4 mM DTT, 1 mM NaPPi, 1 mM dNTPs, 1 U ribonuclease inhibitor, 3.1 μg broad bean poly(A)+-enriched RNA, 21 U AMV reverse transcriptase (Promega Corp) and 0.81 μg Hybrid dT17-adapter primer:

(5'-GACTCGAGTCGACATCGATTTTTTTTTTTTT TTT)(SEQ ID NO: 15)

at 42° C. for 1 hour. The reaction mixture was then diluted to 840 μl with TE (10 mM Tris-HCl pH 8.0, 1 mM EDTA) and stored at −20° C.

A 25-mer oligonucleotide primer (B15):

(5'-GCGGATCCTT[CT]TA[CT]GA[CT]GA[GA]AA [CT]AA)(SEQ ID NO: 18)

was designed based on the sequence of grape PPO.

cDNA was amplified by polymerase chain reaction (PCR) essentially according to the method of. Frohman (2) in a 100

µl reaction mixture containing 10 mM Tris-HCl (pH 9.0 at 25° C.), 50 mM KCl, 1.5 mM MgCl₂ 0.2 mM dNTPs, 0.01% gelatin (w/v), 0.1% Triton X-100, 20 µl diluted 1st. strand cDNA reaction mixture, 2.5 U Taq DNA polymerase (Promema Corp), 100 nM Adapter primer (5'-GACTCGAGTCGACATCG)(SEQ ID NO: 16) and 1 µM B15 primer (described above).

Amplification involved an initial program of 3 cycles of denaturation at 94° C. for 1 min, annealing at 37° C. for 2 min, a slow ramp to 72° C. over 2 min and elongation at 72° C. for 3 min followed by 25 cycles of 94° C. for 1 min, 55° C. for 1 min, and 72° C. for 3 min. Amplified DNA was extracted with phenol/chloroform, precipitated with ethanol and resuspended in TE. DNA was blunt-ended with the Klenow fragment and fractionated on a 2% Nusieve GTG agarose (FMC Bioproducts) gel. A 700 bp fragment was isolated from the gel and ligated into the E=RV site of a Bluescript SK⁺ vector (Stratagene Cloning Systems). Ligated DNA was introduced into *E. coli* DH5. Recombinant clones were screened using a radioactively labelled fragment of the grape PPO clone (GPO1) and a positive clone (designated BPO1) was isolated and sequenced by the dideoxy sequencing method (3).

EXAMPLE 6

Cloning of Apple PPO Genes

Total RNA was isolated from immature apple fruit according to the method of Rezaian and Krake (1). A poly(A)⁺-enriched RNA fraction was obtained using a PolyATtract mRNA kit (Promega corporation).

First strand cDNA was synthesised in a 25 µL reaction mixture containing 50 mM Tris-HCl pH 8.3, p 25 mM KCl, 10 mM MgCl2, 4 mM DTT, 1 mM NaPPi, 1 mM dNTPs, 40 U ribonuclease inhibitor, 1 µg apple poly(A)⁺-enriched RNA, 24 U AMV reverse transcriptase (Promega Corp) and 0.54 µg Hybrid dT17-adapter primer:

(5'-GACTCGAGTCGACATCGATTTTTTTTTTTT TTT)(SEQ ID NO: 15)

at 42° C. for 1 h. The reaction mixture was then diluted to 525 µl with TE (10 mM Tris-HCl pH 8.0, 1 mM EDTA) and stored at −20° C.

A 28-mer oligonucleotide primer (GEN4):

(5'-GCGAATTCGA[AG]GA[TC]ATGGGIAA[TC]TT [TC]TA)(SEQ ID NO: 19)

was designed based on the sequence of grape PPO.

cDNA was amplified by polymerase chain reaction (PCR) essentially according to the method of Frohman (2) in a 100 µl reaction mixture containing 10 mM Tris-HCl (pH 9.0 at 25° C.), 50 mM KCl, 1.5 mM MgCl2, 0.2 mM dNTPs, 0.01% gelatin (w/v), 0.1% Triton X-100, 20 µl diluted 1st. strand cDNA reaction mixture, 2.5 U Tag DNA polymerase (Promega Corp), 100 nM Adapter primer (5'-GACTCGAGTCGACATCG)(SEQ ID NO: 16)

and 1 µM GEN4 primer (described above).

Amplification involved an initial program of 3 cycles of denaturation at 94° C. for 1 min, annealing at 37° C. for 2 min, a slow ramp to 72° C. over 2 min and elongation at 72° C. for 3 min followed by 25 cycles of 94° C. for 1 min, 55° C. for 1 min, and 72° C. for 3 min. Amplified DNA was extracted with phenol/chloroform, precipitated with ethanol and resuspended in TE. DNA was blunt-ended with the Klenow fragment and fractionated on a 2% Nusieve GTG agarose (FMC Bioproducts) gel. A fragment of 1050 bp was isolated from the gel and ligated into the Eco RV site of a Bluescript SK+ vector (Stratagene Cloning Systems). Ligated DNA was introduced into *E. coli* DH5. Recombinant clones were screened using a radioactively labelled fragment of the grape PPO clone (GPO1) and two positive clones (designated pSR7 and pSR8) were isolated and sequenced by the dideoxy sequencing method (3).

EXAMPLE 7

Cloning of Potato PPO Genes

Total RNA was isolated from immature potato tubers according to the method of Logemann et al (4). A poly(A)⁺-enriched RNA fraction was obtained using a PolyATtract mRNA kit (Promega corporation).

First strand cDNA was synthesised in a 25 µl reaction mixture containing 50 mM Tris-HCl pH 8.3, 25 mM KCl, 10 mM MgCl2, 4 mM DTT, 1 mM NaPPi, 1 mM dNTPs, 40 U ribonuclease inhibitor, 1.8 pg potato poly(A)⁺-enriched RNA, 24 U AMV reverse transcriptase (Promega Corp) and 0.54 µg Hybrid dT17-adapter primer:

(5'-GACTCGAGTCGACATCGATTTTTTTTTTTT TTT)(SEQ ID NO: 15)

at 42° C. for 1 h. The reaction mixture was then diluted to 525 µl with TE (10 mM Tris-HCl pH 8.0, 1 mM EDTA) and stored at −20° C.

Two oligonucleotide primers were designed from regions within the sequences of grape and apple PPO:

GEN3: (5'-GCGAATTCTT[TC][TC]TICCITT[TC]CA [TC][AC]G)(SEQ ID NO: 20)

GEN7: (5'-GCGAATTCAA[TC]GTIGA[TC][AC] GIATGTGG)(SEQ ID NO: 21)

cDNA was amplified by the polymerase chain reaction (PCR) essentially according to the method of Frohman (2) in a 100 µl reaction mixture containing 10 mM Tris-HCl (pH 9.0 at 25° C.), 50 mM KCl, 1.5 mM MgCl2, 0.2 mM dNTPs, 0.01% gelatin (w/v), 0.1% Triton X-100, 20 µl diluted 1st. strand cDNA reaction mixture, 2.5 U Taq DNA polymerase (Promega Corp), 100 nM Adapter primer (5'-GACTCGAGTCGACATCG)(SEQ ID NO: 16)

and 1 µM GEN primer (described above).

Amplification involved an initial program of 3 cycles of denaturation at 94° C. for 1 min, annealing at 37° C. for 2 min, a slow ramp to 72° C. over 2 min and elongation at 72° C. for 3 min followed by 25 cycles of 94° C. for 1 min, 55° C. for 1 min, and 72° C. for 3 min. Amplified DNA was extracted with phenol/chloroform, precipitated with ethanol and resuspended in TE. DNA was blunt-ended with the Klenow fragment and fractionated on a 2% Nusieve GTG agarose (FMC Bioproducts) gel. Fragments of 1500 bp and 1000 bp were isolated from the gel and ligated into the Eco RV site of a Bluescript SK+ vector (Stratagene Cloning Systems). Ligated DNA was introduced into *E. coli* DH5. Recombinant clones were selected and three &clones (designated pSRP32, pSRP33, and pSRP72) were isolated and sequenced by the dideoxy sequencing method (3).

cDNA clones containing the 5'-end of potato tuber PPO mRNA were amplified from potato tuber RNA essentially as described in (2), but with nested antisense primers. First strand cDNA was synthesised from potato tuber poly(A)⁺-enriched RNA as described above, but with the Hybrid dT17-adapter primer replaced with potato tuber PPO-specific primer 1:

(5'-GACGGTACATTAGTGTTAAAT)(SEQ ID NO: 27)

complementary to a region 257–278 bases downstream of the 5'-end of pSRP32 and pSRP33. The reaction mixture was diluted to 2 ml with 0.1×TE and centrifuged through a Centricon 30 spin filter (Amicon Corp) at 4000 g for 20 min to remove excess primer. This step was repeated and the remaining liquid concentrated to 12 µl using Speed Vac centrifugation. A poly (dA)-tail sequence was attached at the 3' end of the cDNA strand with Terminal. d Transferase (Promega Corp) in a 20 µl reaction mixture containing 11.5 µl cDNA, 4 µl 5×Tailing Buffer (Promega Corp), 4 µl ATP (1 mM) and 10 U Terminal d Transferase incubated at 37° C. for 5 min followed by 65° C. for 5 min and then diluted to 500 µl with TE. PCR amplification of poly(dA)-tailed cDNA was carried out in a reaction mixture containing 10 mM Tris-HCl (pH 9.0 at 25° C.), 50 mM KCl, 1.5 mM MgCl2, 0.2 mM dNTPs, 0.01% gelatin (w/v), 0.1% Triton X-100, 5 µl diluted 1st. strand cDNA reaction mixture, 1.25 U Taq DNA polymerase (Promega Corp), 200 nM Hybrid dT17-adapter primer and 900 nM potato tuber PPO-specific primer 2

(5'-TGCTCATCAACTGGAGTTGAG)(SEQ ID NO: 25) complementary to a region 233–254 bases downstream of the 5'-end of pSRP32 and pSRP33. Amplification involved 25 cycles of 94° C. for 1 min, 50° C. for 1 min, and 72° C. for 3 min. The resulting fragment was cloned into Bluescript SK+ vector, sequenced as described above and found to contain the predicted region of overlapping sequence with the pSRP32 clone confirming this cDNA clone contained the 5'-end of the potato tuber mRNA.

REFERENCES

1. Rezaian, M. A. and Krake, L. R. (1987). Nucleic acid extraction and vine detection in grapevine. J. Vir. Methods 17: 277–285.
2. Frohman, M. A. (1990) in PCR Protocols: A Guide to Methods and Applications (eds. M. A. Innis, Gelfand, D. H., Sninsky, J. J., White, T. J.) Academic Press, New York pp28–38.
3. Sanger, F., Nicklen, S. and Coulson, A. R. (1977). DNA sequencing with chain-terminating inhibitors. Proc. Natl. Acad. Sci. USA 74: 5463–5467.
4. Logemann, J., Schell, J. and Willmitzer, L. (1987). Improved method for the isolation of RNA from plant tissues. Analytical Biochemistry 163:16–20.

Finally, it is to be understood that various other modifications and/or alterations may be made without departing from the spirit of the present invention as outlined herein.

---

What is claimed is:

1. A method of decreasing the level of PPO activity in a plant comprising
   a) providing
      (i) a DNA construct comprising DNA coding for a polypeptide having plant PPO activity, and
      (ii) a plant tissue;
   b) introducing said DNA construct into said plant tissue; and
   c) regenerating the plant tissue to produce the plant, wherein the DNA coding for a polypeptide having plant PPO activity has a nucleotide sequence that corresponds to
      a nucleotide sequence of DNA from a plant selected from the group consisting of grapevine, apple, and broad bean,
      a nucleotide sequence of DNA from potato selected from the group consisting of: SEQ ID NO: 9, SEQ ID NO: 11, and SEQ ID NO: 13; or
      a nucleotide sequence encoding an amino acid sequence selected from the group consisting of: SEQ ID NO: 10, SEQ ID NO: 12, and SEQ ID NO: 14.

2. The method according to claim 1, wherein the DNA construct comprises a binary vector containing said DNA coding for said PPO polypeptide, and a promoter which is operable in the plant.

3. The method according to claim 1, wherein the DNA construct further comprises a DNA sequence encoding a pre-sequence of a plant PPO gene coding for a transit peptide.

4. An isolated antisense nucleic acid molecule complementary to a DNA comprising nucleotides having a sequence coding for a polypeptide having polyphenol oxidase (PPO) activity, wherein said sequence corresponds to
   a nucleotide sequence of DNA from a plant selected from the group consisting of grapevine, apple, and broad bean,
   a nucleotide sequence of DNA from potato selected from the group consisting of: SEQ ID NO: 9, SEQ ID NO: 11, and SEQ ID NO: 13; or
   a nucleotide sequence encoding an amino acid sequence selected from the group consisting of: SEQ ID NO: 10, SEQ ID NO: 12, and SEQ ID NO: 14.

5. The isolated antisense nucleic acid molecule of claim 4, wherein the nucleic acid is RNA.

6. The isolated antisense nucleic acid molecule of claim 5, wherein the RNA is mRNA.

7. The isolated antisense nucleic acid molecule of claim 4, wherein the nucleic acid is DNA.

8. The isolated antisense nucleic acid molecule of claim 4, wherein the PPO is potato PPO.

9. A transgenic plant transformed with an antisense nucleic acid molecule complementary to a DNA comprising nucleotides having a sequence coding for a polypeptide having polyphenol oxidase (PPO) activity, wherein said sequence corresponds to
   a nucleotide sequence of DNA from a plant selected from the group consisting of grapevine, apple, and broad bean,
   a nucleotide sequence of DNA from potato selected from the group consisting of: SEQ ID NO: 9, SEQ ID NO: 11, and SEQ ID NO 13; or
   a nucleotide sequence encoding an amino acid sequence selected from the group consisting of: SEQ ID NO: 10, SEQ ID NO: 12, and SEQ ID NO: 14.

10. The transgenic plant of claim 9, wherein the plant is potato.

11. An expression vector comprising an antisense nucleic acid molecule complementary to a DNA comprising nucleotides having a sequence coding for a polypeptide having polyphenol oxidase (PPO) activity, wherein said sequence corresponds to
    a nucleotide sequence of DNA from a plant selected from the group consisting of grapevine, apple, and broad bean,
    a nucleotide sequence of DNA from potato selected from the group consisting of: SEQ ID NO: 9, SEQ ID NO: 11, and SEQ ID NO: 13; or
    a nucleotide sequence encoding an amino acid sequence selected from the group consisting of: SEQ ID NO: 10, SEQ ID NO: 12, and SEQ ID NO: 14.

12. Agrobacterium tumefaciens comprising an antisense nucleic acid molecule complementary to a DNA comprising nucleotides having a sequence coding for a polypeptide having polyphenol oxidase (PPO) activity, wherein said sequence corresponds to a nucleotide sequence of DNA from a plant selected from the group consisting of grapevine, apple, and broad bean, a nucleotide sequence of DNA from potato selected from the group consisting of: SEQ ID NO: 9, SEQ ID NO: 11, and SEQ ID NO: 13; or a nucleotide sequence encoding an amino acid sequence selected from the group consisting of: SEQ ID NO: 10, SEQ ID NO: 12, and SEQ ID NO: 14.

13. A method of decreasing the level of PPO expression in a plant cell comprising
a) providing
  a DNA construct comprising an oligonucleotide capable of hybridizing with a sense or antisense strand of a plant polyphenol oxidase (PPO) gene and decreasing expression of such gene in a plant; and
  a plant cell; and
b) introducing said oligonucleotide into said plant cell, thereby decreasing the level of PPO expression in the plant cell,
wherein the plant polyphenol oxidase (PPO) gene comprises nucleotides having a sequence which corresponds to
  a nucleotide sequence of DNA from a plant selected from the group consisting of grapevine, apple, and broad bean,
  a nucleotide sequence of DNA from potato selected from the group consisting of: SEQ ID NO: 9, SEQ ID NO: 11, and SEQ ID NO: 13; or
  a nucleotide sequence encoding an amino acid sequence selected from the group consisting of: SEQ ID NO: 10, SEQ ID NO: 12, and SEQ ID NO: 14.

14. The method according to claim 13, wherein the plant cell is a potato plant cell.

15. The method according to claim 13, wherein the plant cell is a grapevine plant cell.

16. The method according to claim 13, wherein the plant cell is an apple plant cell.

17. The method according to claim 13, wherein the plant cell is a broad bean plant cell.

18. The transgenic plant of claim 9, wherein the plant is grapevine.

19. The transgenic plant of claim 9, wherein the plant is apple.

20. The transgenic plant of claim 9, wherein the plant is broad bean.

21. The transgenic plant of claim 9, wherein the nucleic acid is stably incorporated into the genome of the plant.

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 1990 base pairs
      (B) TYPE: nucleic acid
      (C) STRANDEDNESS: double
      (D) TOPOLOGY: linear (ii) MOLECULE TYPE: cDNA (vii) IMMEDIATE SOURCE:
      (B) CLONE: GPO1 cDNA (ix) FEATURE:
      (A) NAME/KEY: CDS
      (B) LOCATION: 28..1848

(xi) SEQUENCE DESCRIPTION: SEQ ID NO:1:

```
ATCACTCATC ACTCCTCCTC TAAAGCT ATG GCT TCT TTG CCT TGG TCG CTC           51
                             Met Ala Ser Leu Pro Trp Ser Leu
                              1               5

ACA ACC TCC ACC GCC ATC GCC AAC ACC ACC AAC ATT TCA GCC TTC CCA         99
Thr Thr Ser Thr Ala Ile Ala Asn Thr Thr Asn Ile Ser Ala Phe Pro
     10              15                  20

CCT TCT CCC TTG TTT CAA AGG GCT TCT CAT GTC CCC GTA GCC AGA AAC        147
Pro Ser Pro Leu Phe Gln Arg Ala Ser His Val Pro Val Ala Arg Asn
 25              30                  35                  40

CGA AGC CGC AGA TTT GCT CCT AGT AAG GTG TCG TGC AAT TCT GCG AAT        195
Arg Ser Arg Arg Phe Ala Pro Ser Lys Val Ser Cys Asn Ser Ala Asn
             45                  50                  55

GGT GAT CCC AAC TCG GAT TCT ACC TCC GAC GTT CGA GAA ACT TCC TCA        243
Gly Asp Pro Asn Ser Asp Ser Thr Ser Asp Val Arg Glu Thr Ser Ser
             60                  65                  70

GGG AAG TTA GAT AGG AGG AAT GTG CTT CTT GGC ATA GGA GGG CTG TAT        291
Gly Lys Leu Asp Arg Arg Asn Val Leu Leu Gly Ile Gly Gly Leu Tyr
```

-continued

```
            75                  80                  85
GGT GCT GCT GGC GGT CTC GGC GCC ACT AAG CCA TTA GCC TTT GGG GCT    339
Gly Ala Ala Gly Gly Leu Gly Ala Thr Lys Pro Leu Ala Phe Gly Ala
         90                  95                 100

CCC ATC CAG GCA CCG GAT ATA TCC AAG TGT GGT ACC GCC ACC GTG CCT    387
Pro Ile Gln Ala Pro Asp Ile Ser Lys Cys Gly Thr Ala Thr Val Pro
105                 110                 115                 120

GAT GGT GTA ACG CCC ACA AAT TGC TGC CCG CCA GTC ACC ACA AAG ATT    435
Asp Gly Val Thr Pro Thr Asn Cys Cys Pro Pro Val Thr Thr Lys Ile
                125                 130                 135

ATA GAT TTC CAG CTA CCT TCC TCA GGT TCC CCC ATG CGT ACC AGG CCA    483
Ile Asp Phe Gln Leu Pro Ser Ser Gly Ser Pro Met Arg Thr Arg Pro
            140                 145                 150

GCT GCT CAC TTG GTC AGC AAA GAG TAC TTA GCC AAG TAT AAA AAG GCC    531
Ala Ala His Leu Val Ser Lys Glu Tyr Leu Ala Lys Tyr Lys Lys Ala
        155                 160                 165

ATT GAG CTG CAG AAA GCT CTT CCT GAT GAT GAT CCG CGT AGT TTC AAG    579
Ile Glu Leu Gln Lys Ala Leu Pro Asp Asp Asp Pro Arg Ser Phe Lys
170                 175                 180

CAA CAG GCT AAT GTC CAT TGC ACC TAT TGC CAA GGG GCT TAT GAT CAG    627
Gln Gln Ala Asn Val His Cys Thr Tyr Cys Gln Gly Ala Tyr Asp Gln
185                 190                 195                 200

GTT GGG TAT ACC GAC CTA GAA CTC CAG GTT CAT GCT TCA TGG CTT TTC    675
Val Gly Tyr Thr Asp Leu Glu Leu Gln Val His Ala Ser Trp Leu Phe
                205                 210                 215

CTC CCT TTC CAC CGT TAC TAT CTC TAC TTC AAT GAG AGA ATT CTT GCA    723
Leu Pro Phe His Arg Tyr Tyr Leu Tyr Phe Asn Glu Arg Ile Leu Ala
            220                 225                 230

AAG TTG ATC GAC GAT CCC ACC TTC GCT TTG CCC TAT TGG GCT TGG GAT    771
Lys Leu Ile Asp Asp Pro Thr Phe Ala Leu Pro Tyr Trp Ala Trp Asp
        235                 240                 245

AAC CCT GAT GGC ATG TAT ATG CCG ACC ATC TAT GCT AGT TCC CCA TCA    819
Asn Pro Asp Gly Met Tyr Met Pro Thr Ile Tyr Ala Ser Ser Pro Ser
250                 255                 260

TCA CTC TAC GAC GAG AAG CGC AAC GCC AAG CAC CTG CCT CCG ACT GTG    867
Ser Leu Tyr Asp Glu Lys Arg Asn Ala Lys His Leu Pro Pro Thr Val
265                 270                 275                 280

ATC GAT CTC GAC TAC GAT GGC ACC GAA CCC ACA ATC CCT GAT GAC GAA    915
Ile Asp Leu Asp Tyr Asp Gly Thr Glu Pro Thr Ile Pro Asp Asp Glu
                285                 290                 295

CTA AAA ACC GAC AAT CTG GCA ATC ATG TAC AAA CAA ATT GTG TCG GGT    963
Leu Lys Thr Asp Asn Leu Ala Ile Met Tyr Lys Gln Ile Val Ser Gly
            300                 305                 310

GCC ACG ACT CCT AAG CTT TTC CTT GGT TAC CCA TAC CGC GCC GGC GAT    1011
Ala Thr Thr Pro Lys Leu Phe Leu Gly Tyr Pro Tyr Arg Ala Gly Asp
        315                 320                 325

GCG ATT GAC CCT GGA GCG GGT ACC CTT GAG CAC GCC CCA CAT AAT ATA    1059
Ala Ile Asp Pro Gly Ala Gly Thr Leu Glu His Ala Pro His Asn Ile
330                 335                 340

GTC CAC AAA TGG ACT GGT CTT GCT GAT AAG CCT AGT GAG GAC ATG GGA    1107
Val His Lys Trp Thr Gly Leu Ala Asp Lys Pro Ser Glu Asp Met Gly
345                 350                 355                 360

AAC TTC TAT ACT GCC GGC AGA GAC CCC ATA TTC TTC GGT CAC CAC GCC    1155
Asn Phe Tyr Thr Ala Gly Arg Asp Pro Ile Phe Phe Gly His His Ala
                365                 370                 375

AAT GTC GAT CGG ATG TGG AAT ATA TGG AAA ACT ATA GGA GGT AAA AAT    1203
Asn Val Asp Arg Met Trp Asn Ile Trp Lys Thr Ile Gly Gly Lys Asn
            380                 385                 390

AGA AAG GAT TTC ACG GAT ACG GAT TGG CTT GAC GCC ACG TTC GTC TTC    1251
```

-continued

```
Arg Lys Asp Phe Thr Asp Thr Asp Trp Leu Asp Ala Thr Phe Val Phe
    395                 400                 405

TAC GAC GAG AAC AAA CAA CTT GTT AAA GTC AAG GTC TCG GAC TGT GTC      1299
Tyr Asp Glu Asn Lys Gln Leu Val Lys Val Lys Val Ser Asp Cys Val
410                 415                 420

GAC ACT TCC AAG CTG AGA TAC CAA TAT CAG GAT ATT CCT ATT CCA TGG      1347
Asp Thr Ser Lys Leu Arg Tyr Gln Tyr Gln Asp Ile Pro Ile Pro Trp
425                 430                 435                 440

CTA CCA AAA AAT ACG AAG GCC AAA GCG AAG ACG ACC ACC AAA AGT TCC      1395
Leu Pro Lys Asn Thr Lys Ala Lys Ala Lys Thr Thr Thr Lys Ser Ser
                445                 450                 455

AAG TCG GGA GTA GCG AAA GCG GCC GAA CTC CCA AAG ACG ACG ATC AGC      1443
Lys Ser Gly Val Ala Lys Ala Ala Glu Leu Pro Lys Thr Thr Ile Ser
            460                 465                 470

AGC ATC GGA GAC TTC CCA AAA GCT CTT AAC TCA GTG ATA AGA GTA GAA      1491
Ser Ile Gly Asp Phe Pro Lys Ala Leu Asn Ser Val Ile Arg Val Glu
        475                 480                 485

GTT CCA AGG CCA AAG AAA TCA AGA AGC AAG AAG GAG AAA GAG GAT GAG      1539
Val Pro Arg Pro Lys Lys Ser Arg Ser Lys Lys Glu Lys Glu Asp Glu
    490                 495                 500

GAA GAG GTG TTA CTG ATA AAA GGA ATA GAG CTA GAT AGA GAG AAT TTC      1587
Glu Glu Val Leu Leu Ile Lys Gly Ile Glu Leu Asp Arg Glu Asn Phe
505                 510                 515                 520

GTG AAG TTT GAT GTG TAC ATC AAC GAC GAA GAT TAT TCA GTG AGT AGG      1635
Val Lys Phe Asp Val Tyr Ile Asn Asp Glu Asp Tyr Ser Val Ser Arg
                525                 530                 535

CCT AAG AAT AGT GAG TTT GCA GGA AGC TTT GTG AAC GTA CCA CAC AAG      1683
Pro Lys Asn Ser Glu Phe Ala Gly Ser Phe Val Asn Val Pro His Lys
            540                 545                 550

CAT ATG AAA GAA ATG AAG ACG AAG ACC AAT CTG AGG TTC GCG ATA AAT      1731
His Met Lys Glu Met Lys Thr Lys Thr Asn Leu Arg Phe Ala Ile Asn
        555                 560                 565

GAG CTG TTA GAG GAC TTG GGA GCC GAA GAT GAT GAG AGT GTG ATC GTG      1779
Glu Leu Leu Glu Asp Leu Gly Ala Glu Asp Asp Glu Ser Val Ile Val
    570                 575                 580

ACT ATA GTC CCT CGT GCT GGG GGC GAT GAT GTC ACC ATT GGT GGA ATT      1827
Thr Ile Val Pro Arg Ala Gly Gly Asp Asp Val Thr Ile Gly Gly Ile
585                 590                 595                 600

GAG ATC GAG TTT GTT TCC GAT TGATCCCATC TTTCAATGAT TATCCATTAT         1878
Glu Ile Glu Phe Val Ser Asp
                605

ATGTATGTAT CAGGTAAGTC ACATCTTTAT GTGATTAATG GAAAATGTGA GACTTCTCTG    1938

TACTTTCCCG TCAAGTCTTT TATTAATTTA GAGCGTTGGT TAAAAAAAAA AA            1990

(2) INFORMATION FOR SEQ ID NO:2:

(i) SEQUENCE CHARACTERISTICS:
        (A) LENGTH: 607 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ser Leu Pro Trp Ser Leu Thr Thr Ser Thr Ala Ile Ala Asn
1               5                   10                  15

Thr Thr Asn Ile Ser Ala Phe Pro Pro Ser Pro Leu Phe Gln Arg Ala
            20                  25                  30

Ser His Val Pro Val Ala Arg Asn Arg Ser Arg Arg Phe Ala Pro Ser
        35                  40                  45
```

-continued

```
Lys Val Ser Cys Asn Ser Ala Asn Gly Asp Pro Asn Ser Asp Ser Thr
 50                      55                  60

Ser Asp Val Arg Glu Thr Ser Ser Gly Lys Leu Asp Arg Arg Asn Val
 65                      70                  75                  80

Leu Leu Gly Ile Gly Gly Leu Tyr Gly Ala Ala Gly Gly Leu Gly Ala
                     85                  90                  95

Thr Lys Pro Leu Ala Phe Gly Ala Pro Ile Gln Ala Pro Asp Ile Ser
                    100                 105                 110

Lys Cys Gly Thr Ala Thr Val Pro Asp Gly Val Thr Pro Thr Asn Cys
                    115                 120                 125

Cys Pro Pro Val Thr Thr Lys Ile Ile Asp Phe Gln Leu Pro Ser Ser
    130                 135                 140

Gly Ser Pro Met Arg Thr Arg Pro Ala Ala His Leu Val Ser Lys Glu
145                     150                 155                 160

Tyr Leu Ala Lys Tyr Lys Lys Ala Ile Glu Leu Gln Lys Ala Leu Pro
                    165                 170                 175

Asp Asp Asp Pro Arg Ser Phe Lys Gln Gln Ala Asn Val His Cys Thr
                    180                 185                 190

Tyr Cys Gln Gly Ala Tyr Asp Gln Val Gly Tyr Thr Asp Leu Glu Leu
                    195                 200                 205

Gln Val His Ala Ser Trp Leu Phe Leu Pro Phe His Arg Tyr Tyr Leu
    210                 215                 220

Tyr Phe Asn Glu Arg Ile Leu Ala Lys Leu Ile Asp Asp Pro Thr Phe
225                     230                 235                 240

Ala Leu Pro Tyr Trp Ala Trp Asp Asn Pro Asp Gly Met Tyr Met Pro
                    245                 250                 255

Thr Ile Tyr Ala Ser Ser Pro Ser Ser Leu Tyr Asp Glu Lys Arg Asn
                    260                 265                 270

Ala Lys His Leu Pro Pro Thr Val Ile Asp Leu Asp Tyr Asp Gly Thr
                    275                 280                 285

Glu Pro Thr Ile Pro Asp Asp Glu Leu Lys Thr Asp Asn Leu Ala Ile
    290                 295                 300

Met Tyr Lys Gln Ile Val Ser Gly Ala Thr Thr Pro Lys Leu Phe Leu
305                     310                 315                 320

Gly Tyr Pro Tyr Arg Ala Gly Asp Ala Ile Asp Pro Gly Ala Gly Thr
                    325                 330                 335

Leu Glu His Ala Pro His Asn Ile Val His Lys Trp Thr Gly Leu Ala
                    340                 345                 350

Asp Lys Pro Ser Glu Asp Met Gly Asn Phe Tyr Thr Ala Gly Arg Asp
                    355                 360                 365

Pro Ile Phe Phe Gly His His Ala Asn Val Asp Arg Met Trp Asn Ile
    370                 375                 380

Trp Lys Thr Ile Gly Gly Lys Asn Arg Lys Asp Phe Thr Asp Thr Asp
385                     390                 395                 400

Trp Leu Asp Ala Thr Phe Val Phe Tyr Asp Glu Asn Lys Gln Leu Val
                    405                 410                 415

Lys Val Lys Val Ser Asp Cys Val Asp Thr Ser Lys Leu Arg Tyr Gln
                    420                 425                 430

Tyr Gln Asp Ile Pro Ile Pro Trp Leu Pro Lys Asn Thr Lys Ala Lys
                    435                 440                 445

Ala Lys Thr Thr Thr Lys Ser Ser Lys Ser Gly Val Ala Lys Ala Ala
    450                 455                 460
```

```
Glu Leu Pro Lys Thr Thr Ile Ser Ser Ile Gly Asp Phe Pro Lys Ala
465                 470                 475                 480

Leu Asn Ser Val Ile Arg Val Glu Val Pro Arg Pro Lys Lys Ser Arg
                485                 490                 495

Ser Lys Lys Glu Lys Glu Asp Glu Glu Val Leu Leu Ile Lys Gly
            500                 505                 510

Ile Glu Leu Asp Arg Glu Asn Phe Val Lys Phe Asp Val Tyr Ile Asn
                515                 520                 525

Asp Glu Asp Tyr Ser Val Ser Arg Pro Lys Asn Ser Glu Phe Ala Gly
            530                 535                 540

Ser Phe Val Asn Val Pro His Lys His Met Lys Glu Met Lys Thr Lys
545                 550                 555                 560

Thr Asn Leu Arg Phe Ala Ile Asn Glu Leu Leu Glu Asp Leu Gly Ala
                565                 570                 575

Glu Asp Asp Glu Ser Val Ile Val Thr Ile Val Pro Arg Ala Gly Gly
            580                 585                 590

Asp Asp Val Thr Ile Gly Gly Ile Glu Ile Glu Phe Val Ser Asp
            595                 600                 605
```

(2) INFORMATION FOR SEQ ID NO:3:

(i) SEQUENCE CHARACTERISTICS:
        (A) LENGTH: 691 base pairs
        (B) TYPE: nucleic acid
        (C) STRANDEDNESS: double
        (D) TOPOLOGY: linear (ii) MOLECULE TYPE: cDNA (vii) IMMEDIATE SOURCE:
        (B) CLONE: BPO1 clone of broad bean leaf polyphenol
            oxidase (ix) FEATURE:
        (A) NAME/KEY: CDS
        (B) LOCATION: 1..621

(xi) SEQUENCE DESCRIPTION: SEQ ID NO:3:

```
TTT TAC GAT GAG AAC AAG AAT CTT GTT AGG GTT AAT GTG AAG GAC AGT      48
Phe Tyr Asp Glu Asn Lys Asn Leu Val Arg Val Asn Val Lys Asp Ser
 1               5                  10                  15

CTT GAC ACA GAA AAA CTA GGT TAT GCT TAT CAA AAT GTT CCC ATT CCA      96
Leu Asp Thr Glu Lys Leu Gly Tyr Ala Tyr Gln Asn Val Pro Ile Pro
             20                  25                  30

TGG GAA AAT GCT AAA CCT GTG CCA CGA AGA ACA AAA GTA CCA AAA TTG     144
Trp Glu Asn Ala Lys Pro Val Pro Arg Arg Thr Lys Val Pro Lys Leu
         35                  40                  45

GTG GAA GTT GAG GTT AAT GAT GGA AAC TTA AGA AAA TCA CCG ACT ATC     192
Val Glu Val Glu Val Asn Asp Gly Asn Leu Arg Lys Ser Pro Thr Ile
 50                  55                  60

TTA AAA GTT CGA CAA CAG AGT CCA AGA AAA TAC GTT ACG TTT CCA TTG     240
Leu Lys Val Arg Gln Gln Ser Pro Arg Lys Tyr Val Thr Phe Pro Leu
 65                  70                  75                  80

GTT TTG AAT AAT ACA GTG AGT GCT ATT GTG AAG AGG CCA AAG AAA TCA     288
Val Leu Asn Asn Thr Val Ser Ala Ile Val Lys Arg Pro Lys Lys Ser
             85                  90                  95

AGG AGC AAG AAA GAG AAG GAA GAA GAG GAA GAG GTT TTA GTG ATT GAG     336
Arg Ser Lys Lys Glu Lys Glu Glu Glu Glu Glu Val Leu Val Ile Glu
            100                 105                 110

GGG ATT GAG TTT GAT ATG AAT ATA GCC ATT AAG TTT GAT GTT TAT ATT     384
Gly Ile Glu Phe Asp Met Asn Ile Ala Ile Lys Phe Asp Val Tyr Ile
        115                 120                 125
```

```
AAT GAT GAA GAT GCT AAG GTT GGG CCA GGG AAT ACT GAG TTT GCT GGA       432
Asn Asp Glu Asp Ala Lys Val Gly Pro Gly Asn Thr Glu Phe Ala Gly
        130                 135                 140

AGC TTT GTG AAT GTC CCT CAT TCC TCA CAT GGA CAC AGT AAC AAG ATT       480
Ser Phe Val Asn Val Pro His Ser Ser His Gly His Ser Asn Lys Ile
145                 150                 155                 160

ATT ACT TGT TTA AGA CTT GGT ATA ACT GAT TTG TTG GAA GAT TTG GAT       528
Ile Thr Cys Leu Arg Leu Gly Ile Thr Asp Leu Leu Glu Asp Leu Asp
                165                 170                 175

GTC GAA GGC GAT GAT AAT ATT GTG GTT ACA TTG GTT CCA AAA TGT GGG       576
Val Glu Gly Asp Asp Asn Ile Val Val Thr Leu Val Pro Lys Cys Gly
            180                 185                 190

AAT GGA CAA GTC AAA ATC AAT AAC GTC GAG ATA GTG TTT GAA GAT           621
Asn Gly Gln Val Lys Ile Asn Asn Val Glu Ile Val Phe Glu Asp
        195                 200                 205

TGAAAATTTC TACCACTTTG TTATGCACCG TCTGTGTTGA GCGACTTGAG AGGTAGATTT     681

TATGTTTTTT                                                            691

(2) INFORMATION FOR SEQ ID NO:4:

(i) SEQUENCE CHARACTERISTICS:
        (A) LENGTH: 207 amino acids
        (B) TYPE: amino acid
        (D) TOPOLOGY: linear (ii) MOLECULE TYPE: protein (xi) SEQUENCE DESCRIPTION: SEQ ID NO:4:

Phe Tyr Asp Glu Asn Lys Asn Leu Val Arg Val Asn Val Lys Asp Ser
1               5                   10                  15

Leu Asp Thr Glu Lys Leu Gly Tyr Ala Tyr Gln Asn Val Pro Ile Pro
            20                  25                  30

Trp Glu Asn Ala Lys Pro Val Pro Arg Arg Thr Lys Val Pro Lys Leu
        35                  40                  45

Val Glu Val Glu Val Asn Asp Gly Asn Leu Arg Lys Ser Pro Thr Ile
    50                  55                  60

Leu Lys Val Arg Gln Gln Ser Pro Arg Lys Tyr Val Thr Phe Pro Leu
65                  70                  75                  80

Val Leu Asn Asn Thr Val Ser Ala Ile Val Lys Arg Pro Lys Lys Ser
                85                  90                  95

Arg Ser Lys Lys Glu Lys Glu Glu Glu Glu Val Leu Val Ile Glu
            100                 105                 110

Gly Ile Glu Phe Asp Met Asn Ile Ala Ile Lys Phe Asp Val Tyr Ile
        115                 120                 125

Asn Asp Glu Asp Ala Lys Val Gly Pro Gly Asn Thr Glu Phe Ala Gly
    130                 135                 140

Ser Phe Val Asn Val Pro His Ser Ser His Gly His Ser Asn Lys Ile
145                 150                 155                 160

Ile Thr Cys Leu Arg Leu Gly Ile Thr Asp Leu Leu Glu Asp Leu Asp
                165                 170                 175

Val Glu Gly Asp Asp Asn Ile Val Val Thr Leu Val Pro Lys Cys Gly
            180                 185                 190

Asn Gly Gln Val Lys Ile Asn Asn Val Glu Ile Val Phe Glu Asp
        195                 200                 205

(2) INFORMATION FOR SEQ ID NO:5:
```

(i) SEQUENCE CHARACTERISTICS:
    (A) LENGTH: 204 base pairs
    (B) TYPE: nucleic acid
    (C) STRANDEDNESS: double
    (D) TOPOLOGY: linear (ii) MOLECULE TYPE: cDNA (vii) IMMEDIATE SOURCE:
    (B) CLONE: pSR7 clone encoding apple fruit PPO (ix) FEATURE:
    (A) NAME/KEY: CDS
    (B) LOCATION: 1..204

(xi) SEQUENCE DESCRIPTION: SEQ ID NO:5:

```
GAG GAC ATG GGG AAC TTT TAC TCC GCC GGT CGG GAT CCC CTG TTT TAC       48
Glu Asp Met Gly Asn Phe Tyr Ser Ala Gly Arg Asp Pro Leu Phe Tyr
 1               5                  10                  15

GCC CAC CAT TGC AAC GTG GAC CGC ATG TGG AAC GTT TGG AAA ACC CTC       96
Ala His His Cys Asn Val Asp Arg Met Trp Asn Val Trp Lys Thr Leu
            20                  25                  30

GGA GGC AAG CGC AAG GAC CCC ACC GAC ACC GAT TGG CTT GAC GCT GAG      144
Gly Gly Lys Arg Lys Asp Pro Thr Asp Thr Asp Trp Leu Asp Ala Glu
        35                  40                  45

TTT CTG TTC TAC GAT GAA AAC GCC GAG CTT GTG AGC TGT AAA GTT CGG      192
Phe Leu Phe Tyr Asp Glu Asn Ala Glu Leu Val Ser Cys Lys Val Arg
    50                  55                  60

GAC AGC CTC AAC                                                      204
Asp Ser Leu Asn
65
```

(2) INFORMATION FOR SEQ ID NO:6:

(i) SEQUENCE CHARACTERISTICS:
    (A) LENGTH: 68 amino acids
    (B) TYPE: amino acid
    (D) TOPOLOGY: linear (ii) MOLECULE TYPE: protein (xi) SEQUENCE DESCRIPTION: SEQ ID NO:6:

```
Glu Asp Met Gly Asn Phe Tyr Ser Ala Gly Arg Asp Pro Leu Phe Tyr
 1               5                  10                  15

Ala His His Cys Asn Val Asp Arg Met Trp Asn Val Trp Lys Thr Leu
            20                  25                  30

Gly Gly Lys Arg Lys Asp Pro Thr Asp Thr Asp Trp Leu Asp Ala Glu
        35                  40                  45

Phe Leu Phe Tyr Asp Glu Asn Ala Glu Leu Val Ser Cys Lys Val Arg
    50                  55                  60

Asp Ser Leu Asn
65
```

(2) INFORMATION FOR SEQ ID NO:7:

(i) SEQUENCE CHARACTERISTICS:
    (A) LENGTH: 176 base pairs
    (B) TYPE: nucleic acid
    (C) STRANDEDNESS: double
    (D) TOPOLOGY: linear (ii) MOLECULE TYPE: cDNA (vii) IMMEDIATE SOURCE:
    (B) CLONE: pSR8 clone encoding apple fruit PPO (ix) FEATURE:

```
            (A) NAME/KEY: CDS
            (B) LOCATION: 1..174

(xi) SEQUENCE DESCRIPTION: SEQ ID NO:7:

GAG GAT ATG GGG AAT TTT TAC TCT GCG GGG AGG GAT CCG CTG TTT TAC      48
Glu Asp Met Gly Asn Phe Tyr Ser Ala Gly Arg Asp Pro Leu Phe Tyr
 1               5                  10                  15

TCT CAC CAT TCC AAC GTG GAC CGC ATG TGG TCT ATA TAT AAA GAT AAG      96
Ser His His Ser Asn Val Asp Arg Met Trp Ser Ile Tyr Lys Asp Lys
             20                  25                  30

TTG GGA GGT ACG GAC ATA GAA AAA TAC CGA CTG CTG GAC GCA GAG TTC     144
Leu Gly Gly Thr Asp Ile Glu Lys Tyr Arg Leu Leu Asp Ala Glu Phe
         35                  40                  45

TTA TTC TAC GAC GAG AAC AAG AAT CTT CGT GC                          176
Leu Phe Tyr Asp Glu Asn Lys Asn Leu Arg
     50                  55

(2) INFORMATION FOR SEQ ID NO:8:

(i) SEQUENCE CHARACTERISTICS:
        (A) LENGTH: 58 amino acids
        (B) TYPE: amino acid
        (D) TOPOLOGY: linear (ii) MOLECULE TYPE: protein (xi) SEQUENCE DESCRIPTION: SEQ ID NO:8:

Glu Asp Met Gly Asn Phe Tyr Ser Ala Gly Arg Asp Pro Leu Phe Tyr
 1               5                  10                  15

Ser His His Ser Asn Val Asp Arg Met Trp Ser Ile Tyr Lys Asp Lys
             20                  25                  30

Leu Gly Gly Thr Asp Ile Glu Lys Tyr Arg Leu Leu Asp Ala Glu Phe
         35                  40                  45

Leu Phe Tyr Asp Glu Asn Lys Asn Leu Arg
     50                  55

(2) INFORMATION FOR SEQ ID NO:9:

(i) SEQUENCE CHARACTERISTICS:
        (A) LENGTH: 1325 base pairs
        (B) TYPE: nucleic acid
        (C) STRANDEDNESS: double
        (D) TOPOLOGY: linear (ii) MOLECULE TYPE: cDNA (vii) IMMEDIATE SOURCE:
        (B) CLONE: pSRP32 clone encoding potato tuber PPO (ix) FEATURE:
        (A) NAME/KEY: CDS
        (B) LOCATION: 1..1323

(xi) SEQUENCE DESCRIPTION: SEQ ID NO:9:

TTT TTG CCG TTT CAT CGA TGG TAC TTG TAC TTC CAC GAG AGA ATC GTG      48
Phe Leu Pro Phe His Arg Trp Tyr Leu Tyr Phe His Glu Arg Ile Val
 1               5                  10                  15

GGA AAA TTC ATT GAT GAT CCA ACT TTC GCT TTA CCA TAT TGG AAT TGG      96
Gly Lys Phe Ile Asp Asp Pro Thr Phe Ala Leu Pro Tyr Trp Asn Trp
             20                  25                  30

GAC CAT CCA AAA GGT ATG CGT TTT CCT GCC ATG TAT GAT CGT GAA GGG     144
Asp His Pro Lys Gly Met Arg Phe Pro Ala Met Tyr Asp Arg Glu Gly
         35                  40                  45

ACT TCC CTT TTC GAT GTA ACA CGT GAC CAA AGT CAC CGA AAT GGA GCA     192
Thr Ser Leu Phe Asp Val Thr Arg Asp Gln Ser His Arg Asn Gly Ala
```

-continued

```
       50                    55                    60
GTA ATC GAT CTT GGT TTT TTC GGC AAT GAA GTT GAA ACA ACT CAA CTC       240
Val Ile Asp Leu Gly Phe Phe Gly Asn Glu Val Glu Thr Thr Gln Leu
 65                  70                  75                  80

CAG TTG ATG AGC AAT AAT TTA ACA CTA ATG TAC CGT CAA ATG GTA ACT       288
Gln Leu Met Ser Asn Asn Leu Thr Leu Met Tyr Arg Gln Met Val Thr
                 85                  90                  95

AAT GCT CCA TGT CCT CGG ATG TTC TTT GGC GGG CCT TAT GAT CTC GGG       336
Asn Ala Pro Cys Pro Arg Met Phe Phe Gly Gly Pro Tyr Asp Leu Gly
                    100                 105                 110

GTT AAC ACT GAA CTC CCG GGA ACT ATA GAA AAC ATC CCT CAC GGT CCT       384
Val Asn Thr Glu Leu Pro Gly Thr Ile Glu Asn Ile Pro His Gly Pro
            115                 120                 125

GTC CAC ATC TGG TCT GGT ACA GTG AGA GGT TCA ACT TTG CCC AAT GGT       432
Val His Ile Trp Ser Gly Thr Val Arg Gly Ser Thr Leu Pro Asn Gly
    130                 135                 140

GCA ATA TCA AAC GGT GAG AAT ATG GGT CAT TTT TAC TCA GCT GGT TTG       480
Ala Ile Ser Asn Gly Glu Asn Met Gly His Phe Tyr Ser Ala Gly Leu
145                 150                 155                 160

GAC CCG GTT TTC TTT TGC CAT CAC AGC AAT GTG GAT CGG ATG TGG AGC       528
Asp Pro Val Phe Phe Cys His His Ser Asn Val Asp Arg Met Trp Ser
                165                 170                 175

GAA TGG AAA GCG ACA GGA GGG AAA AGA ACG GAT ATC ACA CAT AAA GAT       576
Glu Trp Lys Ala Thr Gly Gly Lys Arg Thr Asp Ile Thr His Lys Asp
            180                 185                 190

TGG TTG AAC TCC GAG TTC TTT TTC TAT GAT GAA AAT GAA AAC CCT TAC       624
Trp Leu Asn Ser Glu Phe Phe Phe Tyr Asp Glu Asn Glu Asn Pro Tyr
        195                 200                 205

CGT GTG AAA GTC AGA GAC TGT TTG GAC ACG AAG AAG ATG GGA TAC GAT       672
Arg Val Lys Val Arg Asp Cys Leu Asp Thr Lys Lys Met Gly Tyr Asp
210                 215                 220

TAC AAA CCA ATT GCC ACA CCA TGG CGT AAC TTC AAG CCC TTA ACA AAG       720
Tyr Lys Pro Ile Ala Thr Pro Trp Arg Asn Phe Lys Pro Leu Thr Lys
            225                 230                 235            240

CCT TCA GCT GGA AAA GTG AAT ACA GCT TCA CTT CCG CCA GCT AGC AAT       768
Pro Ser Ala Gly Lys Val Asn Thr Ala Ser Leu Pro Pro Ala Ser Asn
                245                 250                 255

GTA TTC CCA TTG GCT AAA CTC GAC AAA GCA ATT TCG TTT TCC ATC AAT       816
Val Phe Pro Leu Ala Lys Leu Asp Lys Ala Ile Ser Phe Ser Ile Asn
            260                 265                 270

AGG CCG ACT TCG TCA AGG ACT CAA CAA GAG AAA AAT GCA CAA GAG GAG       864
Arg Pro Thr Ser Ser Arg Thr Gln Gln Glu Lys Asn Ala Gln Glu Glu
        275                 280                 285

ATG TTG ACA TTC AGT AGC ATA AGA TAT GAT AAC AGA GGG TAC ATA AGG       912
Met Leu Thr Phe Ser Ser Ile Arg Tyr Asp Asn Arg Gly Tyr Ile Arg
    290                 295                 300

TTC GAT GTG TTT TCG AAC GTG GAC AAT AAT GTG AAT GCG AAT GAG CTT       960
Phe Asp Val Phe Ser Asn Val Asp Asn Asn Val Asn Ala Asn Glu Leu
305                 310                 315                 320

GAC AAG GCG GAG TTT GCG GGG AGT TAT ACA AGT TTG CCA CAT GTT CAT      1008
Asp Lys Ala Glu Phe Ala Gly Ser Tyr Thr Ser Leu Pro His Val His
                325                 330                 335

AGA GCT GGT GAG ACT AAT CAT ATC GCG ACT GTT GAT TTC CAG CTG GCG      1056
Arg Ala Gly Glu Thr Asn His Ile Ala Thr Val Asp Phe Gln Leu Ala
            340                 345                 350

ATA ACG GAA CTG TTG GAG GAT ATT GGT TTG GAA GAT GAA GAT ACT ATT      1104
Ile Thr Glu Leu Leu Glu Asp Ile Gly Leu Glu Asp Glu Asp Thr Ile
        355                 360                 365

GCG GTG ACT CTG GTG CCA AAG AGA GGT GGT GAA GGT ATC TCC ATT GAA      1152
Ala Val Thr Leu Val Pro Lys Arg Gly Gly Glu Gly Ile Ser Ile Glu
```

```
Ala Val Thr Leu Val Pro Lys Arg Gly Gly Gly Ile Ser Ile Glu
        370                 375                 380

GGT GCG ACG ATC AGT CTT GCA GAT TGT TAA TTA GTC TCT ATT GAA TCT      1200
Gly Ala Thr Ile Ser Leu Ala Asp Cys Xaa Leu Val Ser Ile Glu Ser
385                 390                 395                 400

GCT GAG ATT ACA CTT TGA TGG ATG ATG CTC TGT TTT TGT TTT CTT GTT      1248
Ala Glu Ile Thr Leu Xaa Trp Met Met Leu Cys Phe Cys Phe Leu Val
                405                 410                 415

CTG TTT TTT CCT CTG TTG AAA TCA GCT TTG TTG CTT GAT TTC ATT GAA      1296
Leu Phe Phe Pro Leu Leu Lys Ser Ala Leu Leu Leu Asp Phe Ile Glu
                420                 425                 430

GTT GTT ATT CAA GAA TAA ATC AGT TAC AA                               1325
Val Val Ile Gln Glu Xaa Ile Ser Tyr
                435                 440
```

(2) INFORMATION FOR SEQ ID NO:10:

(i) SEQUENCE CHARACTERISTICS:
        (A) LENGTH: 441 amino acids
        (B) TYPE: amino acid
        (D) TOPOLOGY: linear (ii) MOLECULE TYPE: protein (xi) SEQUENCE DESCRIPTION: SEQ ID NO:10:

```
Phe Leu Pro Phe His Arg Trp Tyr Leu Tyr Phe His Glu Arg Ile Val
1               5                   10                  15

Gly Lys Phe Ile Asp Asp Pro Thr Phe Ala Leu Pro Tyr Trp Asn Trp
                20                  25                  30

Asp His Pro Lys Gly Met Arg Phe Pro Ala Met Tyr Asp Arg Glu Gly
                35                  40                  45

Thr Ser Leu Phe Asp Val Thr Arg Asp Gln Ser His Arg Asn Gly Ala
                50                  55                  60

Val Ile Asp Leu Gly Phe Gly Asn Glu Val Glu Thr Thr Gln Leu
65                  70                  75                  80

Gln Leu Met Ser Asn Asn Leu Thr Leu Met Tyr Arg Gln Met Val Thr
                85                  90                  95

Asn Ala Pro Cys Pro Arg Met Phe Phe Gly Gly Pro Tyr Asp Leu Gly
                100                 105                 110

Val Asn Thr Glu Leu Pro Gly Thr Ile Glu Asn Ile Pro His Gly Pro
                115                 120                 125

Val His Ile Trp Ser Gly Thr Val Arg Gly Ser Thr Leu Pro Asn Gly
                130                 135                 140

Ala Ile Ser Asn Gly Glu Asn Met Gly His Phe Tyr Ser Ala Gly Leu
145                 150                 155                 160

Asp Pro Val Phe Phe Cys His His Ser Asn Val Asp Arg Met Trp Ser
                165                 170                 175

Glu Trp Lys Ala Thr Gly Gly Lys Arg Thr Asp Ile Thr His Lys Asp
                180                 185                 190

Trp Leu Asn Ser Glu Phe Phe Tyr Asp Glu Asn Glu Asn Pro Tyr
                195                 200                 205

Arg Val Lys Val Arg Asp Cys Leu Asp Thr Lys Lys Met Gly Tyr Asp
                210                 215                 220

Tyr Lys Pro Ile Ala Thr Pro Trp Arg Asn Phe Lys Pro Leu Thr Lys
225                 230                 235                 240

Pro Ser Ala Gly Lys Val Asn Thr Ala Ser Leu Pro Pro Ala Ser Asn
                245                 250                 255
```

```
Val Phe Pro Leu Ala Lys Leu Asp Lys Ala Ile Ser Phe Ser Ile Asn
            260                 265                 270

Arg Pro Thr Ser Ser Arg Thr Gln Gln Glu Lys Asn Ala Gln Glu Glu
            275                 280                 285

Met Leu Thr Phe Ser Ser Ile Arg Tyr Asp Asn Arg Gly Tyr Ile Arg
            290                 295                 300

Phe Asp Val Phe Ser Asn Val Asp Asn Asn Val Asn Ala Asn Glu Leu
305                 310                 315                 320

Asp Lys Ala Glu Phe Ala Gly Ser Tyr Thr Ser Leu Pro His Val His
                325                 330                 335

Arg Ala Gly Glu Thr Asn His Ile Ala Thr Val Asp Phe Gln Leu Ala
            340                 345                 350

Ile Thr Glu Leu Leu Glu Asp Ile Gly Leu Glu Asp Glu Asp Thr Ile
            355                 360                 365

Ala Val Thr Leu Val Pro Lys Arg Gly Glu Gly Ile Ser Ile Glu
            370                 375                 380

Gly Ala Thr Ile Ser Leu Ala Asp Cys Xaa Leu Val Ser Ile Glu Ser
385                 390                 395                 400

Ala Glu Ile Thr Leu Xaa Trp Met Met Leu Cys Phe Cys Phe Leu Val
                405                 410                 415

Leu Phe Phe Pro Leu Leu Lys Ser Ala Leu Leu Leu Asp Phe Ile Glu
            420                 425                 430

Val Val Ile Gln Glu Xaa Ile Ser Tyr
            435                 440

(2) INFORMATION FOR SEQ ID NO:11:

(i) SEQUENCE CHARACTERISTICS:
        (A) LENGTH: 1315 base pairs
        (B) TYPE: nucleic acid
        (C) STRANDEDNESS: double
        (D) TOPOLOGY: linear (ii) MOLECULE TYPE: cDNA (vii) IMMEDIATE SOURCE:
        (B) CLONE: pSRP33 clone encoding potato tuber PPO (ix) FEATURE:
        (A) NAME/KEY: CDS
        (B) LOCATION: 1..1314

(xi) SEQUENCE DESCRIPTION: SEQ ID NO:11:

TTC TTG CCG TTC CAC CGA TGG TAC TTA TAC TTC TAC GAG AGA ATA TTG        48
Phe Leu Pro Phe His Arg Trp Tyr Leu Tyr Phe Tyr Glu Arg Ile Leu
 1               5                  10                  15

GGA AAA CTC ATC GAT GAT CCA ACT TTC GCT TTA CCA TAT TGG AAT TGG        96
Gly Lys Leu Ile Asp Asp Pro Thr Phe Ala Leu Pro Tyr Trp Asn Trp
            20                  25                  30

GAT CAT CCA AAG GGC ATG CGT TTA CCT CCC ATG TTC GAT CGT GAA GGA       144
Asp His Pro Lys Gly Met Arg Leu Pro Pro Met Phe Asp Arg Glu Gly
        35                  40                  45

ACT TCT ATT TAC GAC GAA AGG CGT AAT CAA CAA GTC CGT AAC GGA ACC       192
Thr Ser Ile Tyr Asp Glu Arg Arg Asn Gln Gln Val Arg Asn Gly Thr
    50                  55                  60

GTT ATG GAT CTT GGT TCA TTT GGG GAC AAG GTC CAA ACA ACT CAA CTC       240
Val Met Asp Leu Gly Ser Phe Gly Asp Lys Val Gln Thr Thr Gln Leu
65                  70                  75                  80

CAG TTG ATG AGC AAT AAT TTA ACA CTA ATG TAC CGT CAA ATG GTA ACT       288
Gln Leu Met Ser Asn Asn Leu Thr Leu Met Tyr Arg Gln Met Val Thr
                85                  90                  95
```

```
AAT GCT CCA TGT CCT CTT TTG TTC TTC GGT GCG CCT TAC GTT CTT GGG      336
Asn Ala Pro Cys Pro Leu Leu Phe Phe Gly Ala Pro Tyr Val Leu Gly
            100                 105                 110

AAT AAC GTC GAA GCC CCG GGA ACC ATT GAA AAC ATC CCT CAT ATA CCT      384
Asn Asn Val Glu Ala Pro Gly Thr Ile Glu Asn Ile Pro His Ile Pro
            115                 120                 125

GTC CAT ATT TGG GCT GGT ACA GTA CGT GGT TCA ACA TTT CCT AAT GGT      432
Val His Ile Trp Ala Gly Thr Val Arg Gly Ser Thr Phe Pro Asn Gly
        130                 135                 140

GAT ACG TCA TAC GGT GAG GAT ATG GGT AAT TTC TAC TCA GCT GGT TTA      480
Asp Thr Ser Tyr Gly Glu Asp Met Gly Asn Phe Tyr Ser Ala Gly Leu
145                 150                 155                 160

GAC CCG GTT TTC TAT TGC CAC CAC GGC AAT GTG GAC CGT ATG TGG AAT      528
Asp Pro Val Phe Tyr Cys His His Gly Asn Val Asp Arg Met Trp Asn
                165                 170                 175

GAA TGG AAG GCA ATA GGA GGT AAG AGA AGG GAT TTA TCA GAA AAA GAT      576
Glu Trp Lys Ala Ile Gly Gly Lys Arg Arg Asp Leu Ser Glu Lys Asp
            180                 185                 190

TGG TTG AAC TCT GAG TTC TTC TTT TAT GAT GAA AAC AAA AAG CCT TAC      624
Trp Leu Asn Ser Glu Phe Phe Phe Tyr Asp Glu Asn Lys Lys Pro Tyr
            195                 200                 205

CGT GTG AAA GTC CGA GAC TGT TTG GAC GCG AAG AAA ATG GGG TAC GAT      672
Arg Val Lys Val Arg Asp Cys Leu Asp Ala Lys Lys Met Gly Tyr Asp
        210                 215                 220

TAC GCA CCA ATG CCA ACT CCA TGG CGT AAC TTC AAA CCA AAA ACA AAG      720
Tyr Ala Pro Met Pro Thr Pro Trp Arg Asn Phe Lys Pro Lys Thr Lys
225                 230                 235                 240

GCA TCA GTA GGG AAA GTG AAT ACA ACT ACA CTC CCC CCA GTG AAC AAG      768
Ala Ser Val Gly Lys Val Asn Thr Thr Thr Leu Pro Pro Val Asn Lys
                245                 250                 255

GTA TTC CCA CTC ACG AAG ATG GAT AAA GCC ATT TCA TTT TCC ATC AAT      816
Val Phe Pro Leu Thr Lys Met Asp Lys Ala Ile Ser Phe Ser Ile Asn
            260                 265                 270

AGG CCT GCT TCA TCG CGG ACT CAA CAA GAG AAA AAT GAA CAA GAG GAG      864
Arg Pro Ala Ser Ser Arg Thr Gln Gln Glu Lys Asn Glu Gln Glu Glu
            275                 280                 285

ATG TTA ACG TTC GAT AAC ATA AAA TAT GAT AAT AGA GGG TAT ATA AGG      912
Met Leu Thr Phe Asp Asn Ile Lys Tyr Asp Asn Arg Gly Tyr Ile Arg
290                 295                 300

TTC GAT GTA TTT CTG AAC GTG GAT AAC AAT GTG AAT GCG AAT GAG CTT      960
Phe Asp Val Phe Leu Asn Val Asp Asn Asn Val Asn Ala Asn Glu Leu
305                 310                 315                 320

GAT AAG GCA GAG TTC GCG GGG AGT TAT ACT AGT TTG CCA CAT GTT CAC     1008
Asp Lys Ala Glu Phe Ala Gly Ser Tyr Thr Ser Leu Pro His Val His
                325                 330                 335

AGA GTT GGC GAG AAT GAT CAT ACC GCG ACT GTT ACT TTC CAG CTG GCG     1056
Arg Val Gly Glu Asn Asp His Thr Ala Thr Val Thr Phe Gln Leu Ala
            340                 345                 350

ATA ACA GAA CTG TTG GAG GAC ATT GGT TTG GAA GAT GAA GAG ACT ATT     1104
Ile Thr Glu Leu Leu Glu Asp Ile Gly Leu Glu Asp Glu Glu Thr Ile
            355                 360                 365

GCG GTG ACT CTG GTA CCA AAG AAA GGT GGT GAA GGT ATC TCC ATT GAA     1152
Ala Val Thr Leu Val Pro Lys Lys Gly Gly Glu Gly Ile Ser Ile Glu
        370                 375                 380

AAT GTG GAG ATC AAG CTT CTG GAT TGT TAA GTA CGT TCT CAA TTG AAT     1200
Asn Val Glu Ile Lys Leu Leu Asp Cys Xaa Val Arg Ser Gln Leu Asn
385                 390                 395                 400

CTG CTG AGA TTA CAA CTT TGA TAT GTT TTT TAC TTT TGT TTT TCC ATG     1248
Leu Leu Arg Leu Gln Leu Xaa Tyr Val Phe Tyr Phe Cys Phe Ser Met
```

```
                   405                 410                 415
TAA CTT TTC CTG TTG AAA TCA GCT TGA TGC TTG ATT TCC TTG GAG TTG    1296
Xaa Leu Phe Leu Leu Lys Ser Ala Xaa Cys Leu Ile Ser Leu Glu Leu
            420                 425                 430

TTA TTC ACT AAT AAA ATC A                                          1315
Leu Phe Thr Asn Lys Ile
        435
```

(2) INFORMATION FOR SEQ ID NO:12:

(i) SEQUENCE CHARACTERISTICS:
        (A) LENGTH: 438 amino acids
        (B) TYPE: amino acid
        (D) TOPOLOGY: linear (ii) MOLECULE TYPE: protein (xi) SEQUENCE DESCRIPTION: SEQ ID NO:12:

```
Phe Leu Pro Phe His Arg Trp Tyr Leu Tyr Phe Tyr Glu Arg Ile Leu
 1               5                  10                  15

Gly Lys Leu Ile Asp Asp Pro Thr Phe Ala Leu Pro Tyr Trp Asn Trp
            20                  25                  30

Asp His Pro Lys Gly Met Arg Leu Pro Pro Met Phe Asp Arg Glu Gly
        35                  40                  45

Thr Ser Ile Tyr Asp Glu Arg Arg Asn Gln Gln Val Arg Asn Gly Thr
    50                  55                  60

Val Met Asp Leu Gly Ser Phe Gly Asp Lys Val Gln Thr Thr Gln Leu
65                  70                  75                  80

Gln Leu Met Ser Asn Asn Leu Thr Leu Met Tyr Arg Gln Met Val Thr
                85                  90                  95

Asn Ala Pro Cys Pro Leu Leu Phe Phe Gly Ala Pro Tyr Val Leu Gly
            100                 105                 110

Asn Asn Val Glu Ala Pro Gly Thr Ile Glu Asn Ile Pro His Ile Pro
        115                 120                 125

Val His Ile Trp Ala Gly Thr Val Arg Gly Ser Thr Phe Pro Asn Gly
    130                 135                 140

Asp Thr Ser Tyr Gly Glu Asp Met Gly Asn Phe Tyr Ser Ala Gly Leu
145                 150                 155                 160

Asp Pro Val Phe Tyr Cys His His Gly Asn Val Asp Arg Met Trp Asn
                165                 170                 175

Glu Trp Lys Ala Ile Gly Gly Lys Arg Arg Asp Leu Ser Glu Lys Asp
            180                 185                 190

Trp Leu Asn Ser Glu Phe Phe Phe Tyr Asp Glu Asn Lys Lys Pro Tyr
        195                 200                 205

Arg Val Lys Val Arg Asp Cys Leu Asp Ala Lys Lys Met Gly Tyr Asp
    210                 215                 220

Tyr Ala Pro Met Pro Thr Pro Trp Arg Asn Phe Lys Pro Lys Thr Lys
225                 230                 235                 240

Ala Ser Val Gly Lys Val Asn Thr Thr Thr Leu Pro Pro Val Asn Lys
                245                 250                 255

Val Phe Pro Leu Thr Lys Met Asp Lys Ala Ile Ser Phe Ser Ile Asn
            260                 265                 270

Arg Pro Ala Ser Ser Arg Thr Gln Gln Glu Lys Asn Glu Gln Glu Glu
        275                 280                 285

Met Leu Thr Phe Asp Asn Ile Lys Tyr Asp Asn Arg Gly Tyr Ile Arg
    290                 295                 300
```

```
Phe Asp Val Phe Leu Asn Val Asp Asn Asn Val Asn Ala Asn Glu Leu
305                 310                 315                 320

Asp Lys Ala Glu Phe Ala Gly Ser Tyr Thr Ser Leu Pro His Val His
                325                 330                 335

Arg Val Gly Glu Asn Asp His Thr Ala Thr Val Thr Phe Gln Leu Ala
                340                 345                 350

Ile Thr Glu Leu Leu Glu Asp Ile Gly Leu Glu Asp Glu Thr Ile
            355                 360                 365

Ala Val Thr Leu Val Pro Lys Lys Gly Glu Gly Ile Ser Ile Glu
        370                 375                 380

Asn Val Glu Ile Lys Leu Leu Asp Cys Xaa Val Arg Ser Gln Leu Asn
385                 390                 395                 400

Leu Leu Arg Leu Gln Leu Xaa Tyr Val Phe Tyr Phe Cys Phe Ser Met
                405                 410                 415

Xaa Leu Phe Leu Leu Lys Ser Ala Xaa Cys Leu Ile Ser Leu Glu Leu
                420                 425                 430

Leu Phe Thr Asn Lys Ile
            435
```

(2) INFORMATION FOR SEQ ID NO:13:

(i) SEQUENCE CHARACTERISTICS:
        (A) LENGTH: 892 base pairs
        (B) TYPE: nucleic acid
        (C) STRANDEDNESS: double
        (D) TOPOLOGY: linear (ii) MOLECULE TYPE: cDNA (vii) IMMEDIATE SOURCE:
        (B) CLONE: pID5RACE4 clone encoding potato tuber PPO (ix) FEATURE:
        (A) NAME/KEY: CDS
        (B) LOCATION: 28..891

(xi) SEQUENCE DESCRIPTION: SEQ ID NO:13:

```
TTTTTTTTTA TTCAAAAGCT AGCAATA ATG GCA AGC TTG TGC AAT AGT TGT            51
                              Met Ala Ser Leu Cys Asn Ser Cys
                                1               5

AGT ACA TCC CTC AAA ACT CCT TTT ACT TCT TCC TCC ACT TCT TTA ACT         99
Ser Thr Ser Leu Lys Thr Pro Phe Thr Ser Ser Ser Thr Ser Leu Thr
    10                  15                  20

TCC ACT CCT AAA CCC TCT CAA CTT TTC ATC CAT GGA AAA CGT AAC CAA        147
Ser Thr Pro Lys Pro Ser Gln Leu Phe Ile His Gly Lys Arg Asn Gln
25                  30                  35                  40

ATG TTC AAA GTT TCA TGC ATG GTT ACC AAT AAT AAC GGT GAC CAA AAC        195
Met Phe Lys Val Ser Cys Met Val Thr Asn Asn Asn Gly Asp Gln Asn
                45                  50                  55

CAA AAC GTT GAA ACG AAT TCT GTT GAT CGA AGA AAT GTT CTT CTT GGC        243
Gln Asn Val Glu Thr Asn Ser Val Asp Arg Arg Asn Val Leu Leu Gly
            60                  65                  70

TTA GGT GGT CTT TAT GGT GTT GCT AAT GCT ATA CCA TTA GCT GCA TCC        291
Leu Gly Gly Leu Tyr Gly Val Ala Asn Ala Ile Pro Leu Ala Ala Ser
        75                  80                  85

GCT ACT CCA TCT CCA CCT CCT GAT CTC TCG TCT TGT AGT ATA GCC AGG        339
Ala Thr Pro Ser Pro Pro Pro Asp Leu Ser Ser Cys Ser Ile Ala Arg
    90                  95                 100

ATT AAC GAA ACT CAT GTG GTG CCG TAC AGT TGT TGC GCG CCT AAG CCT        387
Ile Asn Glu Thr His Val Val Pro Tyr Ser Cys Cys Ala Pro Lys Pro
105                 110                 115                 120
```

-continued

```
GAT GAT ATG GAG AAA GTT CCG TAT TAC AAG TTC CCT TCT ATG ACT AAG        435
Asp Asp Met Glu Lys Val Pro Tyr Tyr Lys Phe Pro Ser Met Thr Lys
            125                 130                 135

CTC CGT GTT CGT CAG CCT GCT CAT GAA GCT AAT GAG GAG TAT ATT GCC        483
Leu Arg Val Arg Gln Pro Ala His Glu Ala Asn Glu Glu Tyr Ile Ala
            140                 145                 150

AAG TAC AAT TTG GCG GTT AGC AAG ATG AGG GAT CTT GAT AAG ACA CAA        531
Lys Tyr Asn Leu Ala Val Ser Lys Met Arg Asp Leu Asp Lys Thr Gln
            155                 160                 165

CCT TTA AAC CCT ATT GGT TTT AAG CAA CAA GCT AAT ATA CAT TGT GCT        579
Pro Leu Asn Pro Ile Gly Phe Lys Gln Gln Ala Asn Ile His Cys Ala
    170                 175                 180

TAT TGT AAC GGT GCT TAT AGA ATT GGT GGC AAA GAG TTA CAA GTT CAT        627
Tyr Cys Asn Gly Ala Tyr Arg Ile Gly Gly Lys Glu Leu Gln Val His
185                 190                 195                 200

AAT TCT TGG CTT TTC TTC CCG TTC CAT AGA TGG TAC TTG TAC TTC TAC        675
Asn Ser Trp Leu Phe Phe Pro Phe His Arg Trp Tyr Leu Tyr Phe Tyr
                205                 210                 215

GAG AGA ATC GTG GGA AAA TTC ATT GAT GAT GCA ACT TTC GCT TTG CCA        723
Glu Arg Ile Val Gly Lys Phe Ile Asp Asp Ala Thr Phe Ala Leu Pro
            220                 225                 230

TAT TGG AAT TGG GAC CAT CCA AAG GGT ATG CGT TTT CCT GCC ATG TAT        771
Tyr Trp Asn Trp Asp His Pro Lys Gly Met Arg Phe Pro Ala Met Tyr
            235                 240                 245

GAT CGT GAA GGG ACT TCC CTT TTC GAT GTA ACA CGT GAC CAA AGT CAC        819
Asp Arg Glu Gly Thr Ser Leu Phe Asp Val Thr Arg Asp Gln Ser His
    250                 255                 260

CGA AAT GGA GCA GTA ATC GAT CTT GGT TTT ATC GGC AAT GAA GTC GAA        867
Arg Asn Gly Ala Val Ile Asp Leu Gly Phe Ile Gly Asn Glu Val Glu
265                 270                 275                 280

ACA ACT CAA CTC CAG TTG ATG AGC A                                      892
Thr Thr Gln Leu Gln Leu Met Ser
                285
```

(2) INFORMATION FOR SEQ ID NO:14:

(i) SEQUENCE CHARACTERISTICS:
        (A) LENGTH: 288 amino acids
        (B) TYPE: amino acid
        (D) TOPOLOGY: linear (ii) MOLECULE TYPE: protein (xi) SEQUENCE DESCRIPTION: SEQ ID NO:14:

```
Met Ala Ser Leu Cys Asn Ser Cys Ser Thr Ser Leu Lys Thr Pro Phe
 1               5                   10                  15

Thr Ser Ser Ser Thr Ser Leu Thr Ser Thr Pro Lys Pro Ser Gln Leu
            20                  25                  30

Phe Ile His Gly Lys Arg Asn Gln Met Phe Lys Val Ser Cys Met Val
        35                  40                  45

Thr Asn Asn Asn Gly Asp Gln Asn Gln Asn Val Glu Thr Asn Ser Val
    50                  55                  60

Asp Arg Arg Asn Val Leu Gly Leu Gly Gly Leu Tyr Gly Val Ala
65                  70                  75                  80

Asn Ala Ile Pro Leu Ala Ala Ser Ala Thr Pro Ser Pro Pro Asp
                85                  90                  95

Leu Ser Ser Cys Ser Ile Ala Arg Ile Asn Glu Thr His Val Val Pro
                100                 105                 110

Tyr Ser Cys Cys Ala Pro Lys Pro Asp Asp Met Glu Lys Val Pro Tyr
        115                 120                 125
```

```
Tyr Lys Phe Pro Ser Met Thr Lys Leu Arg Val Arg Gln Pro Ala His
    130                 135                 140
Glu Ala Asn Glu Glu Tyr Ile Ala Lys Tyr Asn Leu Ala Val Ser Lys
145                 150                 155                 160
Met Arg Asp Leu Asp Lys Thr Gln Pro Leu Asn Pro Ile Gly Phe Lys
                165                 170                 175
Gln Gln Ala Asn Ile His Cys Ala Tyr Cys Asn Gly Ala Tyr Arg Ile
                180                 185                 190
Gly Gly Lys Glu Leu Gln Val His Asn Ser Trp Leu Phe Phe Pro Phe
            195                 200                 205
His Arg Trp Tyr Leu Tyr Phe Tyr Glu Arg Ile Val Gly Lys Phe Ile
    210                 215                 220
Asp Asp Ala Thr Phe Ala Leu Pro Tyr Trp Asn Trp Asp His Pro Lys
225                 230                 235                 240
Gly Met Arg Phe Pro Ala Met Tyr Asp Arg Glu Gly Thr Ser Leu Phe
                245                 250                 255
Asp Val Thr Arg Asp Gln Ser His Arg Asn Gly Ala Val Ile Asp Leu
                260                 265                 270
Gly Phe Ile Gly Asn Glu Val Glu Thr Thr Gln Leu Gln Leu Met Ser
            275                 280                 285
```

(2) INFORMATION FOR SEQ ID NO:15:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GACTCGAGTC GACATCGATT TTTTTTTTTT TTTTT       35

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GACTCGAGTC GACATCG       17

(2) INFORMATION FOR SEQ ID NO:17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: Primer utilized for amplification of grape
            cDNA (ix) FEATURE:
        (A) NAME/KEY: modified_base
        (B) LOCATION: 3..24

(D) OTHER INFORMATION: /mod_base= i (xi) SEQUENCE DESCRIPTION: SEQ ID NO:17:

CCNATNCAGG CNCCNGATAT NNCNAAGTGT GG                                32

(2) INFORMATION FOR SEQ ID NO:18:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(vii) IMMEDIATE SOURCE:
         (B) CLONE: Primer utilized for amplification of bean
             cDNA (xi) SEQUENCE DESCRIPTION: SEQ ID NO:18:

GCGGATCCTT YTAYGAYGAR AAYAA                                        25

(2) INFORMATION FOR SEQ ID NO:19:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: DNA (genomic)

(vii) IMMEDIATE SOURCE:
         (B) CLONE: Primer utilized for  amplification of apple
             cDNA (ix) FEATURE:
         (A) NAME/KEY: modified_base
         (B) LOCATION: 20
         (D) OTHER INFORMATION: /mod_base= i (xi) SEQUENCE DESCRIPTION: SEQ ID NO:19:

GCGAATTCGA RGAYATGGGN AAYTTYTA                                     28

(2) INFORMATION FOR SEQ ID NO:20:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: modified_base
         (B) LOCATION: 14..17
         (D) OTHER INFORMATION: /mod_base= i (xi) SEQUENCE DESCRIPTION: SEQ ID NO:20:

GCGAATTCTT YYTNCCNTTY CAYMG                                        25

(2) INFORMATION FOR SEQ ID NO:21:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (genomic)

(ix) FEATURE:
            (A) NAME/KEY: modified_base
            (B) LOCATION: 14..20
            (D) OTHER INFORMATION: /mod_base= i (xi) SEQUENCE DESCRIPTION: SEQ ID NO:21:

GCGAATTCAA YGTNGAYMGN ATGTGG                                              26

(2) INFORMATION FOR SEQ ID NO:22:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:22:

AATCTTTGTG GTGACTGGCG                                                     20

(2) INFORMATION FOR SEQ ID NO:23:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:23:

GACGGTACAT TAGTCTTAAA T                                                   21

(2) INFORMATION FOR SEQ ID NO:24:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:24:

ACCATCAGGC ACGGTGGCGG                                                     20

(2) INFORMATION FOR SEQ ID NO:25:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:25:

TGCTCATCAA CTGGAGTTGA G                                                   21

(2) INFORMATION FOR SEQ ID NO:26:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (xi) SEQUENCE DESCRIPTION: SEQ ID NO:26:

```
Ala Pro Ile Gln Ala Pro Asp Ile Ser Lys Cys Gly Thr Ala Thr Val
 1               5                  10                  15
Pro Asp Gly Val Thr Pro
            20
```

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GACGGTACAT TAGTGTTAAA T                      21